(12) United States Patent
Van Haaften

(10) Patent No.: US 12,018,006 B2
(45) Date of Patent: Jun. 25, 2024

(54) METHOD OF PRODUCING EPD AND ANALOGUES THEREOF

(71) Applicant: Caroline Van Haaften, Leiden (NL)

(72) Inventor: Caroline Van Haaften, Leiden (NL)

( * ) Notice: Subject to any disclaimer, the term of this patent is extended or adjusted under 35 U.S.C. 154(b) by 829 days.

(21) Appl. No.: 16/620,219

(22) PCT Filed: Jun. 8, 2018

(86) PCT No.: PCT/NL2018/050377
§ 371 (c)(1),
(2) Date: Dec. 6, 2019

(87) PCT Pub. No.: WO2018/226102
PCT Pub. Date: Dec. 13, 2018

(65) Prior Publication Data
US 2021/0078965 A1 Mar. 18, 2021

(30) Foreign Application Priority Data
Jun. 8, 2017 (NL) .................................. 2019035

(51) Int. Cl.
*C07D 307/92* (2006.01)
*C07C 49/553* (2006.01)
*C07C 57/26* (2006.01)
*C07C 69/003* (2006.01)

(52) U.S. Cl.
CPC .......... *C07D 307/92* (2013.01); *C07C 49/553* (2013.01); *C07C 57/26* (2013.01); *C07C 69/003* (2013.01)

(58) Field of Classification Search
CPC .................................................. C07D 307/83
See application file for complete search history.

(56) References Cited

FOREIGN PATENT DOCUMENTS

WO    2012005581 A1    1/2012

OTHER PUBLICATIONS

Baiocchi et al., Arenes From Alkanes or Cycloalkanes Through Dehydration or Rearrangement with Pyridinium Chloride, Gazzetta Chimica Italiana, 1985, 115:199-216.
Bohlmann et al., Eudesmanolides, Guaianolides, Germacranolides and Elemanolides from *Zinnia* Species, Phytochemistry, 1981, 20(7):1623-1630.
Buchschacher et al., (S)-8a-Methyl-3,4,8,8a-Tetrahydro-1,6(2H, 7H)-Naphthalenedione [1,6(2H, 7H)-Naphthalenedione, 3,4,8,8a-tetrahydro-8a-methyl-, (S)-], Organic Syntheses, Coll. vol. 7, p. 368 (1990); vol. 63, p. 37 (1985).
Carneiro et al., A Ring Contraction Strategy Toward a Diastereoselective Total Synthesis of (+)-Bakkenolide A, Journal of Organic Chemistry, 2010, 75(9):2877-2882.
Carneiro et al., A Ring Contraction Strategy Toward a Diastereoselective Total Synthesis of (+)-Bakkenolide A, Supporting Information, pp. S1-S13.
Duke et al., Efficient Isolation of an Anti-Cancer Sesquiterpene Lactone from Calomeria Amaranthoides by Steam Distillation, Green and Sustainable Chemistry, 2011, 1:123-127.
Piers et al., Total Synthesis of (±)-Eremophilenolide, Chemical Communications, 1971, p. 614.
Piers et al., Total Synthesis of Eremophilane-type Sesquiterpenoids:(±)-Eremophilenolide,(±)-Tetrahydroligularenolide, and (±)-Aristolochene, Canadian Journal of Chemistry, 1973, 51(13):2166-2173.
Tanaka et al., Chemische Untersuchungen der Inhaltsstoffe von Xanthium canadense Mill, Chemical and Pharmaceutical Bulletin, 1976, 24(6):1419-1421.
Van Haaften-Day et al., Flow Cytometric and Morphological Studies of Ovarian Carcinoma Cell Lines and Xenografts, Cancer Research, 1983, 43:3725-3731.
Van Haaften et al., Synergistic Effects of the Sesquiterpene Lactone, EPD, with Cisplatin and Paclitaxel in Ovarian Cancer Cells, Journal of Experimental & Clinical Cancer Research, 2015, 34:38, 9 pages.
Zoretic et al., Sesquiterpene Synthesis. Studies Relating to the Synthesis of (+−)-Dugesialactone, Journal of Organic Chemistry, 1982, 47(7):1327-1329.
PCT International Search Report, PCT/NL2018/050377, dated Aug. 13, 2018, 3 pages.
Ozaki et al., Total Synthesis of Sophorapterocarpan A, Maackiain, and Anhydropisatin: Application of a 1, 3-Michael-Claisen Annulation to Aromatic Synthesis, Journal of the Chemical Society, Perkin Transactions, 1989, 17:1219-1224.
Shono et al., Synthesis of a-Methylene Carbonyl Compounds, Organic Synthetic Chemistry, 1981, 39(5):358-373.
Japan Patent Office, Notice of Reasons for Refusal, Application No. 2020-518388, dated Jun. 4, 2022, 12 pages.

*Primary Examiner* — Alicia L Otton

(57) ABSTRACT

The present invention is directed to methods for the preparation of eremophila-1(10)-11(13)-dien-12,8β-olide (EPD) and analogues thereof.

15 Claims, 8 Drawing Sheets

METHOD OF PRODUCING EPD AND ANALOGUES THEREOF

CROSS-REFERENCE TO RELATED APPLICATIONS

This application is a national stage entry of PCT International Application No. PCT/NL2018/050377, filed Jun. 8, 2018, which claims priority to Netherlands Application No. 2019035, filed Jun. 8, 2017, both of which are incorporated herein by reference as if set forth in their entirety for all purposes.

FIELD OF THE INVENTION

The invention is in the field of producing safe and effective medicaments for the treatment of human patients. More in particular, the present invention relates to methods of synthetically producing sesquiterpene lactone preparations useful for the treatment of cancer in human subjects.

BACKGROUND OF THE INVENTION

The biogenesis and chemistry of terpenoids is a well-studied scientific field. This is partly due to the fact that terpenoids have many uses in our society. Terpenoids can be extracted from diverse plant origins by means of distillation. New naturally occurring terpenoids are constantly isolated. They play a role in traditional herbal remedies and are under investigation for antibacterial, antineoplastic, and other pharmaceutical functions. Plant terpenoids are used extensively for their aromatic qualities. The important bioactivity of these molecules ensures continued interest in their synthesis. Understanding the biosynthesis of these molecules may aid in the development of new approaches to functional terpenoids and a better understanding of the relationship to function.

Previously, an anti-cancer agent, xanthanodine or eremophila-1(10)-11(13)-dien-12,8β-olide (EPD), was found to exhibit potent cytotoxic effects towards ovarian cancer and not towards normal cells (WO2012/005581). The compound was isolated from *Calomeria amaranthoides* by steam distillation as described by Duke, Van Haaften, & Tran, 2011 (Green Sustainable Chem Vol (1):123-7). EPD has been assigned the following structure:

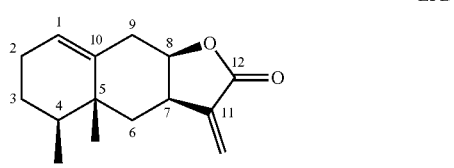

EPD

It is noted that the absolute stereochemistry of EPD has not yet been determined and that the indication of the stereochemistry at carbons 4, 5, 7 and 8 in the above formula may indicate the relative stereochemistry only.

Current methods for obtaining EPD involve isolation from natural sources. In order to produce this sesquiterpene lactone at high purity without depending on its native source, the *Calomeria amaranthoides* plant, and to produce sufficient material for clinical studies into the anti-cancer effect of EPD, it is desired to provide a method to produce EPD by synthetic means. It is further desired that such a method enables the production of EPD analogues which can not be easily obtained from EPD that is isolated from biological sources.

SUMMARY OF THE INVENTION

The present inventors have now found a manner to produce EPD and its analogues by a synthetic route. The advantage of such a synthetic route of medicament production is that the quality of the product can be better controlled, and contamination of the product can be prevented. This means that regulatory requirements for the production of EPD can now be fulfilled. In addition, the present invention enables the preparation of EPD analogues which can not be easily obtained from EPD that is isolated from biological sources.

DETAILED DESCRIPTION OF THE INVENTION

Figure 1A:
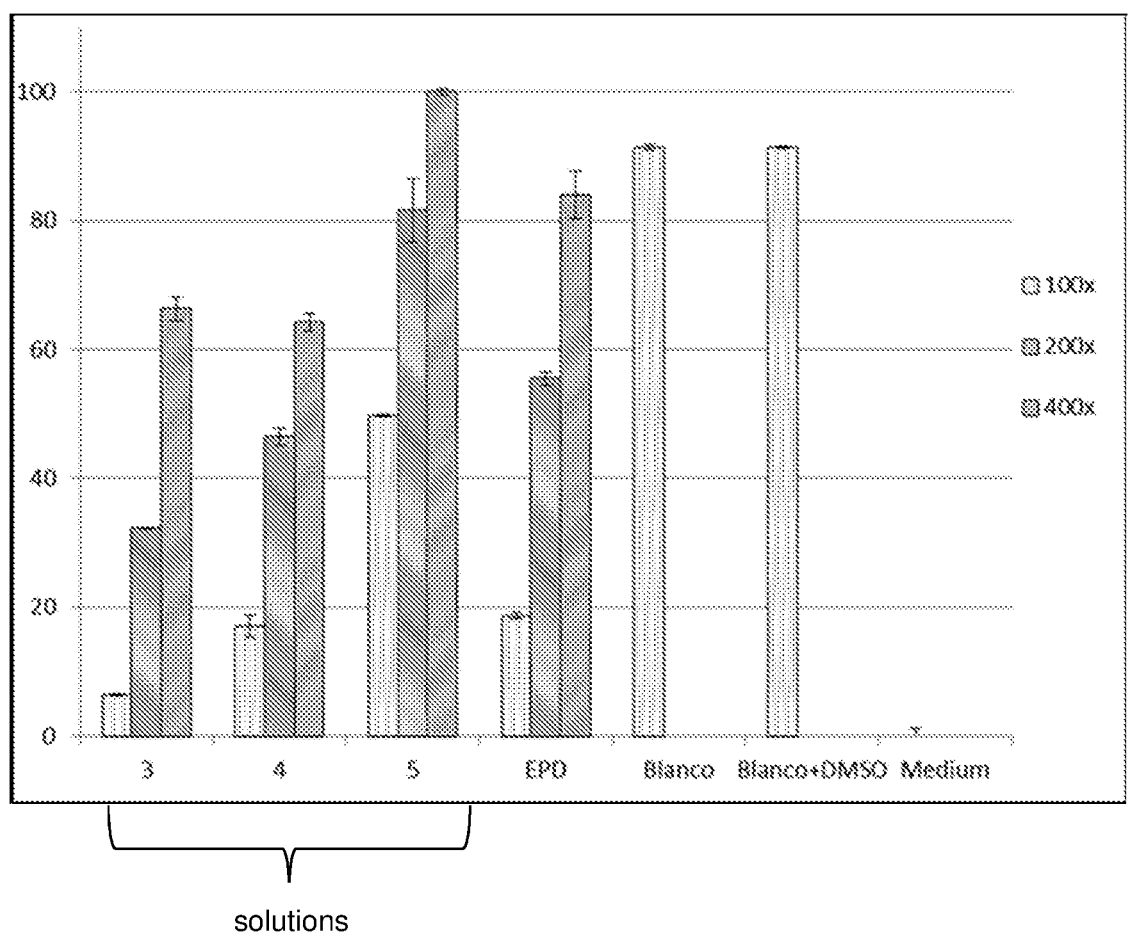
FIG. 1 shows the results of the experiments as described in Example 19, wherein the in vitro cytotoxic activity of a number of inventive compounds and reference compounds was tested in JC cancer cell line (see Van Haaften-Day et al. Cancer Res. 1983 for the JC cancer cell lines).

The invention is directed to a method for the production of EPD or an analogue thereof according to formula I

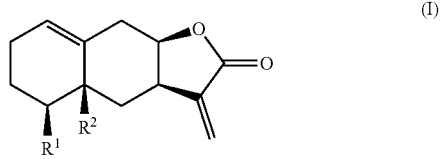

(I)

wherein $R^1$ and $R^2$ are independently selected from $R^3$, $SR^3$, $SO_2R^3$, $N(R^3)_2$, $C(O)NR^3$, $NC(O)R^3$, $OR^3$, $CO_2R$, $OC(O)R^3$, Cl, F, Br or I, preferably $OR^3$ or $R^3$ and $R^3$ is selected from H, $C_1$-$C_8$ hydrocarbyl or poly(alkene oxide), preferably from H or methyl;

said method comprising converting an intermediate compound of formula II

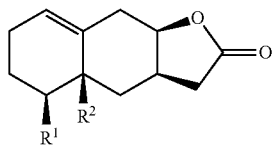

II to EPD or an analogue of formula I by one or more steps comprising methylation.

With 'independently selected from' is meant that the substituents concerned may be the same or may be different. It also means that the group $R^3$ may be the same or may be different for $R^1$ and $R^2$.

The poly(alkene oxide) is preferably a poly(ethylene oxide) and typically provides a better solubility of the compound and improved pharmacokinetics.

In a preferred embodiment, $R^2$ is selected from H, $C_1$-$C_8$ hydrocarbyl. In a more preferred embodiment of the present invention, $R^1$ and $R^2$ are both methyl. In yet another preferred embodiment, $R^1$ is hydrogen and $R^2$ is methyl.

In a typical embodiment, the methylenation of the intermediate compound of formula II comprises deprotonation followed by successively a reaction with ethyl formate and a reaction with a formaldehyde donor such as paraformaldehyde.

A particular advantage of the present invention is the high degree of control over the stereoselectivity and the stereospecificity of the method steps in the production process. In addition, the present invention enables the preparation of analogues of EPD as indicated with $R^1$ and $R^2$ in formula I. Unless specifically defined otherwise, the substituents $R^1$ and $R^2$ of all formulae and compounds disclosed herein are in accordance with those for the compound of formula I.

The preparation of the intermediate compound of formula II is a further aspect of the present invention. For the preparation of EPD and analogues therefore according to formula I, the carbon atom 7 (see the structure of EPD above) is configured cis with respect to the other carbon stereocenters (carbon atoms 4, 5 and 8). The present inventors surprisingly found that the cis configuration of the core of EPD and its analogues can be obtained by reducing the compound of formula III to the intermediate compound of formula II, in accordance with Scheme 1.

Scheme 1

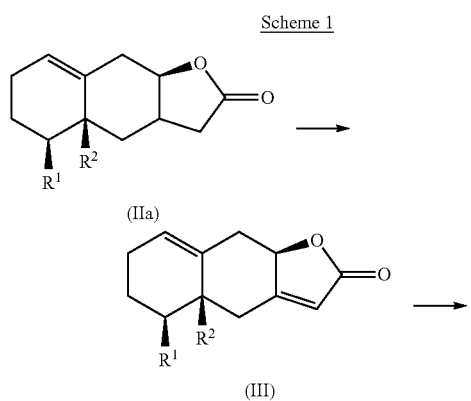

-continued

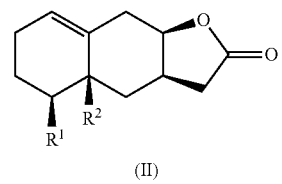

(II)

Good results in terms of yield and stereospecificity were obtained in an embodiment wherein reducing the compound of formula III to the intermediate compound of formula II is carried out with a hydride donor. Preferably, the hydride donor is a borohydride, more preferably sodium borohydride. In a preferred embodiment, the reduction of the compound of formula III is carried out in the presence of a catalyst, preferably a Lewis acid, more preferably a nickel halide such as nickel(II) chloride.

The compound of formula III is preferably obtained by converting a compound of formula IIa as illustrated in Scheme 1. The compound of formula IIa as illustrated in Scheme 1 may comprise a mixture of stereoisomeric compounds.

In the present context, in case a formula used herein comprises a chiral center of which the chirality is not indicated, said formula is meant to illustrate all variations of the chirality of said chiral center and concomitantly is meant to illustrate all individual stereoisomeric compounds and mixtures thereof. In addition, in case a formula used herein comprises a chiral center of which the chirality is indicated, this indication of the chirality is meant to illustrate the relative chirality of the chiral center with respect to other stereogenic centers within the same formula or compound, unless explicitly indicated otherwise. Thus, unless explicitly described otherwise, the structural formulae that illustrate the compounds described herein, illustrate both enantiomers of said compounds and/or diastereoisomers thereof, if applicable. Accordingly, for sake of completeness it is noted that the word 'compound' in reference to a particular formula, may refer to a plurality of compounds, i.e. a mixture of several isomers such as enantiomers or diastereoisomers. Thus, for example, the compound of formula IIa refers to all individual compounds and combinations thereof having the absolute stereochemistry as illustrated with formulae IIaa, IIab, IIba and IIbb in Scheme 2.

Scheme 2

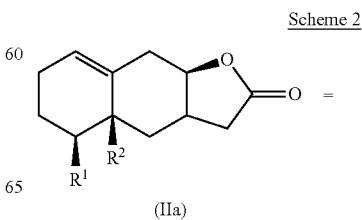

(IIa)

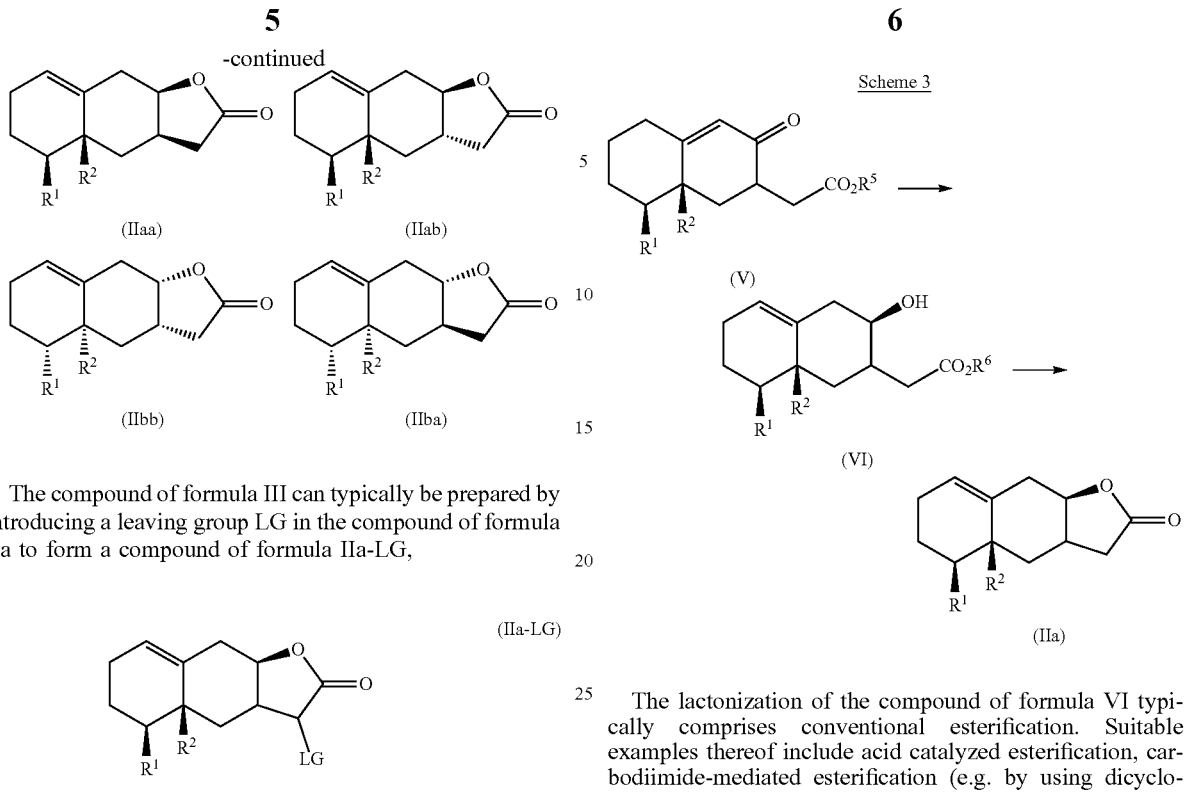

The compound of formula III can typically be prepared by introducing a leaving group LG in the compound of formula IIa to form a compound of formula IIa-LG, followed by eliminating the leaving group to form the compound of formula III. The leaving group can be selected from the group consisting of a selenium compound, halide, ester or sulfonate, preferably a selenium compound such as benzeneselenyl or halide such as bromide, chloride or iodide.

Preferably, the leaving group LG is introduced in the compound of formula IIa by deprotonation (e.g. with a sterically hindered strong base such as lithium di-isopropyl amide or potassium bis(trimethylsilyl)amide) and a reaction with a leaving group donor. In the embodiments wherein the leaving group comprises bromide, the leaving group donor may be bromine or N-bromosuccinimide or carbon tetrabromide.

In the embodiments wherein the leaving group is a selenium compound such as benzeneselenyl, the leaving group donor may be a selenating agent such as a phenyl selenating agent. Elimination of the selenium compound can be carried out via an (in situ) oxidation. Introduction and elimination of the selenium compound can also be referred to as selenoxide elimination.

In a preferred embodiment of the present invention, the compound of formula IIa is obtained by converting a compound of formula V, preferably through a lactonization of a compound of formula VI, as illustrated in Scheme 3, wherein $R^5$ and $R^6$ are independently selected from H, $C_1$-$C_6$ alkyl or a cation such as ammonium, an alkali metal ion or an alkaline earth metal ion. Examples of suitable alkali metal and alkaline earth metal ions include Li, Na, K, Ca, Mg, and the like. The ester moiety of the compound of formula V (as indicated with $R^5$) may be exchanged by another moeity or remain the same. Preferably, said ester moiety remains the same.

The lactonization of the compound of formula VI typically comprises conventional esterification. Suitable examples thereof include acid catalyzed esterification, carbodiimide-mediated esterification (e.g. by using dicyclohexyl carbodiimide and 4-dimethylaminopyridine) and the like.

The conversion of the compound of formula V to the compound of formula VI may typically be carried out by an acetylation to form a compound of formula VIII, followed by a reduction (e.g. with sodium borohydride) as illustrated in Scheme 4.

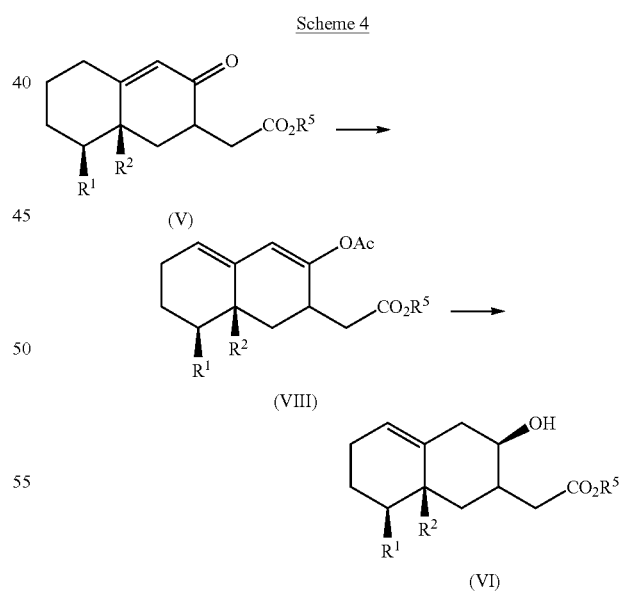

The compound of formula V can typically be obtained by a Robinson annulation of a compound of formula IX with methylvinylketone and an acid, preferably methanesulfonic acid and/or benzenesulfonic acid, as illustrated in Scheme 5. In Scheme 5, the symbol === indicates a single or double bond, and $R^1$ of compound IX can be selected from O, NH or S if === is a double bond.

Scheme 5

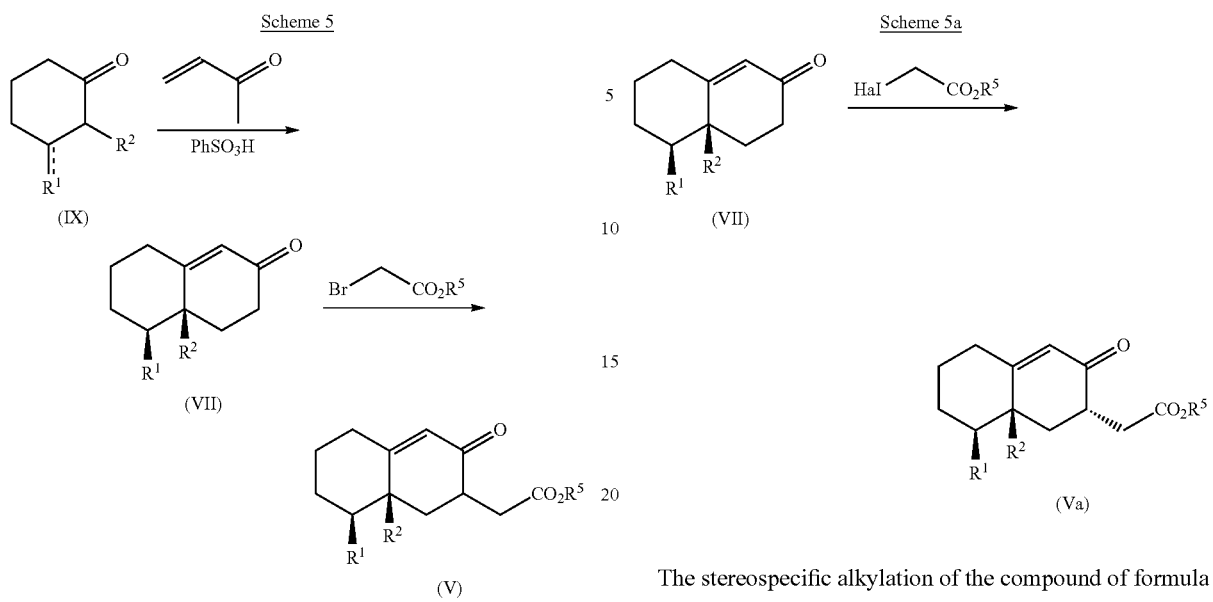

Scheme 5a

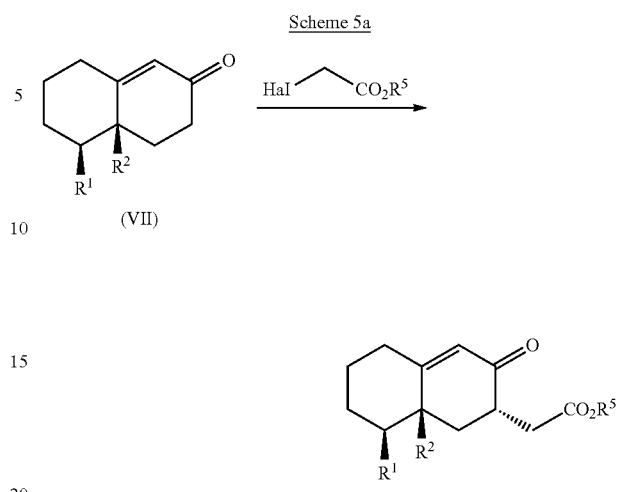

The general Robinson annulation of certain compounds of formula IX, for instance for those compounds of formula I wherein $R^1$ and $R^2$ are both methyl, is known and typically carried out with strong acids such as sulfuric acid. However, these known processes are generally associated with low yields. The present inventors surprisingly found that the yield of the Robinson annulation can be improved by using an acid that is less strong than sulfuric acid, for instance by using organic acids.

Accordingly, a particular aspect of the present invention is the Robinson annulation, preferably of a compound of formula IX, with methylvinylketone, preferably in the presence of an acid having a $pK_a$ of −2.9 or higher. Particular good results were obtained by using an organic acid, preferably an organic sulfonic acid such as benzenesulfonic acid (having a $pK_a$ of −2.8) and methanesulfonic acid (having a $pK_a$ of −1.9).

The compound of formula V can be obtained by alkylation of the compound of formula VII. The alkylation can be carried out by deprotonation of the α-hydrocarbon of the enone, followed by addition of an electrophilic reagent such as a an alkyl haloacetate as indicated in Scheme 5. Particularly suitable alkyl haloacetates include alkyl bromoacetates such as tert-butyl bromoacetate and ethyl bromoacetate. Generally, as illustrated in Scheme 5a, the alkylation proceeds essentially stereospecific meaning that the stereochemistry of the newly generated stereogenic carbon atom is determined by the stereochemistry of one or more of the other stereogenic carbon atoms, i.e. one or both of the carbons being connected to $R^1$ and $R^2$. The stereospecific alkylation can typically be obtained by using a alkyl bromoacetate such as ethyl bromoacetate or t-butyl bromoacetate.

The stereospecific alkylation of the compound of formula VII results in an essentially diastereomerically pure compound of formula Va without the separation of the diastereoisomers as represented by formula V.

With essentially diastereomerically pure is herein meant a typical diastereomeric ratio (dr) of ratio of at least 90:10, preferably at least 95:5, more preferably at least 99:1 of the desired diastereoisomer with respect to the other diastereoisomers.

The diastereomerically purity of the compound of formula Va can typically be maintained during the subsequent steps, by using the same chemical steps as described herein above for the convertion of the compound of formula V into that of formulae VIII and VI (cf. Scheme 4). In other words, also the compounds of formulae VIII, VI and IIa can be obtained essentially diastereomerically pure, as illustrated in Scheme 5b with the formulae VIIIa, VIa and IIax.

Scheme 5b

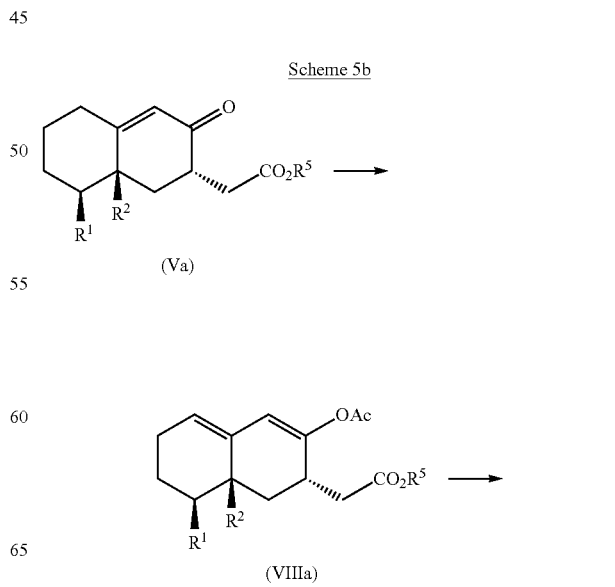

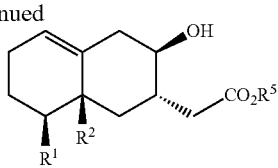

(VIa)

↓

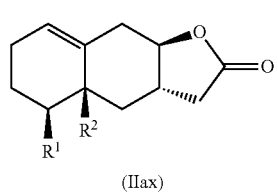

(IIax)

The stereospecifity of the alkylation of the compound of formula VII is preferred but not required for the preparation of the compounds of formulae I or II since the chirality of the newly generated stereogenic center is typically lost during the preparation of the intermediate compound of formula II (cf. compound of formula III in Scheme 1). However, preference for the stereospecific alkylation arises from the finding that the compound of formula Va may be advantageously used in the enantiomerically pure preparation of the compound of formulae I and II, as is described in detail herein-below. Surprisingly, it was found that the diastereomerically pure compound of formula VIIIa does not hamper the formation of the desired stereochemistry of the hydroxy moeity of the compound of formula VIa by reduction of the compound of formula VIIIa with for instance sodium borohydride.

The present invention advantageously enables the synthesis of natural EPD and the synthesis of racemic EPD, which comprises (natural) EPD its enantiomer.

Even though the absolute stereochemistry of EPD has not yet been resolved, the present method enables the preparation of EPD and its enantiomer since the present inventors have found that EPD is the compound in the racemic mixture that elutes as the second compound from the chiral HPLC column of the type Phenomenex Lux Amylose-2 (3.0×150 mm; 3 μm) using a mixture of $CO_2$ and methanol as the mobile phase.

A further aspect of the present invention is directed to the EPD analogue according to formula I

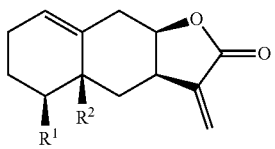

(I)

wherein $R^1$ is selected from H, $C_2$-$C_8$ hydrocarbyl or poly (alkene oxide), $SR^3$, $SO_2R^3$, $N(R^3)_2$, $C(O)NR^3$, $NC(O)R^3$, $OR^3$, $CO_2R^3$, $OC(O)R^3$, Cl, F, Br or I, preferably H or $OR^3$;
$R^2$ is selected from $R^4$, $SR^4$, $SO_2R^4$, $N(R^4)_2$, $C(O)NR^4$, $NC(O)R^4$, $OR^4$, $CO_2R^4OC(O)R^4$, Cl, F, Br or I, preferably $R^4$, H or $OR^4$; and;
$R^3$ and $R^4$ are independently selected from H, $C_1$-$C_8$ hydrocarbyl or poly(alkene oxide), preferably methyl.

Preferably, $R^1$ and $R^2$ are both methyl or $R^1$ is hydrogen and $R^2$ is methyl.

It was surprisingly found that the analogues of EPD of formula I wherein $R^1$ is H and $R^2$ is methyl can also be associated with anti-tumoral activity. Accordingly, said EPD analogue of formula I for use in a medicament, preferably for use in a method of treating cancer is a particular aspect of the present invention.

In a particular embodiment, $R^1$ of the compound of formula I is selected from poly(alkene oxide), $SR^3$, $SO_2R^3$, $N(R^3)_2$, $C(O)NR^3$, $NC(O)R^3$, $OR^3$, $CO_2R^3$ or $OC(O)R^3$, and $R^3$ is selected from H or poly(alkene oxide). This embodiment is found to be particularly advantageous to improve the solubility and the pharmakinetic properties of the EPD analogue.

The compounds wherein $R^1$ is selected from poly(alkene oxide), $SR^3$, $SO_2R^3$, $N(R^3)_2$, $C(O)NR^3$, $NC(O)R^3$, $OR^3$, $CO_2R^3$ or $OC(O)R^3$, can be obtained by reacting the compound of IX, wherein === is a double bond and $R^1$ is selected from O, NH or S. For instance, in a particular embodiment, compound IX is the Wieland-Miescher ketone which can be enantioselectively converted to the corresponding compound of formula VII as illustrated in Scheme 6 (see also Paul Buchschacher et al. *Organic Syntheses*, Coll. Vol. 7, p. 368 (1990); Vol. 63, p. 37 (1985)).

Scheme 6

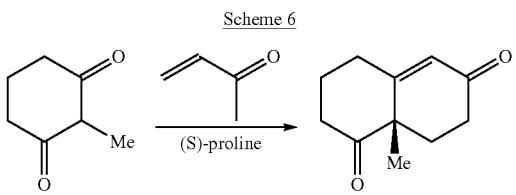

Another aspect of the present invention is directed to the intermediate compounds suitable for preparation of EPD or an analogue thereof in a method according to the present invention.

A particular embodiment of this aspect of the invention is the intermediate compound of formula II

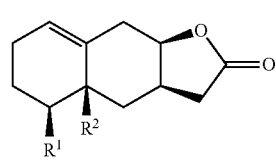

II wherein $R^1$ are independently selected from $R^3$, $SR^3$, $SO_2R^3$, $N(R^3)_2$, $C(O)NR^3$, $NC(O)R^3$, OR, $CO_2R^3$, $OC(O)R^3$, Cl, Br, F, I, preferably $OR^3$ or $R^3$ and;
$R^3$ is selected from H, $C_1$-$C_8$ hydrocarbyl or poly(alkene oxide).

Another particular embodiment is the intermediate compound according to one of formulae IIa, IIax, III, V, Va, VI, VIa, VIII, or VIIIa

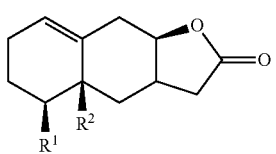

IIa

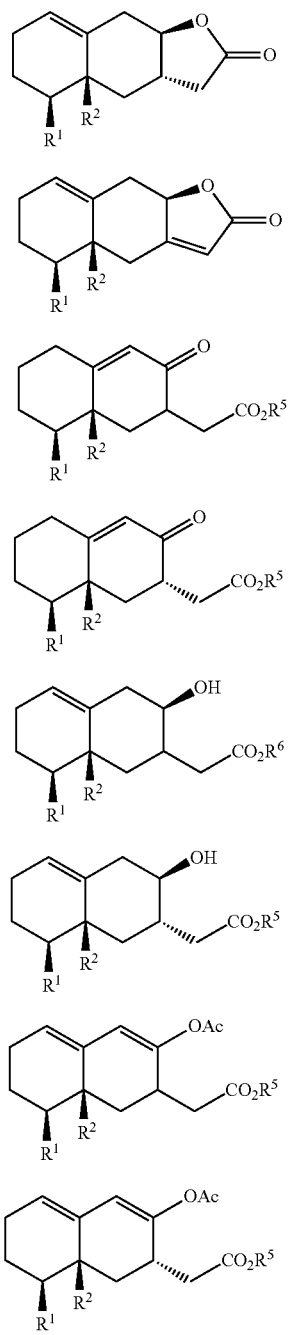

(IIax)

(III)

(V)

(Va)

(VI)

(VIa)

(VIII)

(VIIIa)

wherein $R^1$ is selected from H, $C_2$-$C_8$ hydrocarbyl or poly(alkene oxide), $SR^3$, $SO_2R^3$, $N(R^3)_2$, $C(O)NR^3$, $NC(O)R^3$, $OR^3$, $CO_2R^3$, $OC(O)R^3$, F, Cl, Br or I, preferably H or $OR^3$; $R^2$ is selected from $R^4$, $SR^4$, $SO_2R^4$, $N(R^4)_2$, $C(O)NR^4$, $NC(O)R^4$, $OR^4$, $CO_2R^4 OC(O)R^4$, Cl, F, Br or I, preferably $R^4$, H or $OR^4$;

$R^3$ and $R^4$ are independently selected from H, $C_1$-$C_8$ hydrocarbyl or poly(alkene oxide), preferably methyl; and $R^5$ and $R^6$ are selected from H, $C_1$-$C_6$ alkyl or a cation such as ammonium, an alkali metal ion or an alkaline earth metal ion.

In a preferred embodiment, the compound of formula I has the absolute stereochemistry as represented with formula I or vise-versa (since the absolute stereochemistry of EPD has not yet been resolved, vide supra). The method of the present invention preferably comprises the enantioselective preparation of the compound of formula I.

The steps of the method described herein-above typically comprise stereospecific conversion of the respective compounds. Accordingly, by providing an enantiomerically pure isomer of the intermediate compounds en route to EPD and its analogues, enantiomerically pure EPD and its analogues can be prepared by the present invention. The enantiomers of EPD and its analogues can also be obtained in this way. For instance, the enantioselective synthesis of the Wieland-Miescher ketone as described herein above (see also Paul Buchschacher et al. *Organic Syntheses*, Coll. Vol. 7, p. 368 (1990); Vol. 63, p. 37 (1985)) enables the enantioselective synthesis in accordance with the present invention of all compounds described herein. In particular, the enantioselective synthesis of the compound of formula VII, wherein $R^1$ and $R^2$ are each methyl can be carried out as described in Carneiro et al. *Journal of Organic Chemistry* 75 (2010) 2877-2882.

Another process for the enantioselective preparation of the compound of formula I or the intermediate compounds described herein includes resolution via diastereomeric salt crystallization, which is another aspect of the present invention. For this aspect of the invention, it is preferred that the compound of formula VI is obtained essentially diastereoisomerically pure as the compound of formula VIa. The compound of formula VIa can be obtained by the stereospecific alkylation of the compound of formula VII to the compound of formula Va, and a subsequent acetylation and reduction as described herein-above and illustrated in Scheme 5b.

The inventors surprisingly found that only one of the enantiomers of the intermediate compound according to formula VIa wherein $R^6$ is H can be selectively crystallized by using a chiral amine such as an phenylalkylamine. In this respect, it is emphasized that, as explained herein above in general, formula VIa illustrates a mixture of the enantiomers VIab and VIba as illustrated in Scheme 7 below. Thus, although the drawings of the compounds of formulae VIa and VIab are identical, the formulae represent two different type of compounds: formula VIa represents a racemic mixture of the compound of formulae VIab and VIba, and formula VIab represent an enantiomerically pure compound.

Scheme 7

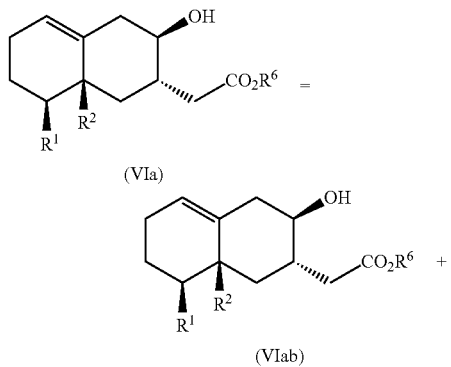

-continued

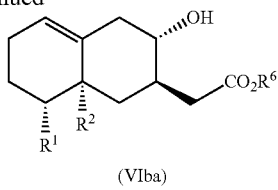

(VIba)

Surprisingly, by using the chiral amine, a salt can be formed and precipitated with either the enantiomer of formula VIab or the enantiomer of formula VIba, while the other enantiomer (of which no salt precipitates) remains in solution, as illustrated in Scheme 8. Which particular enantiomer forms the salt and which particular isomers remain in solution can be decided by selecting the appropriate chirality of the chiral amine.

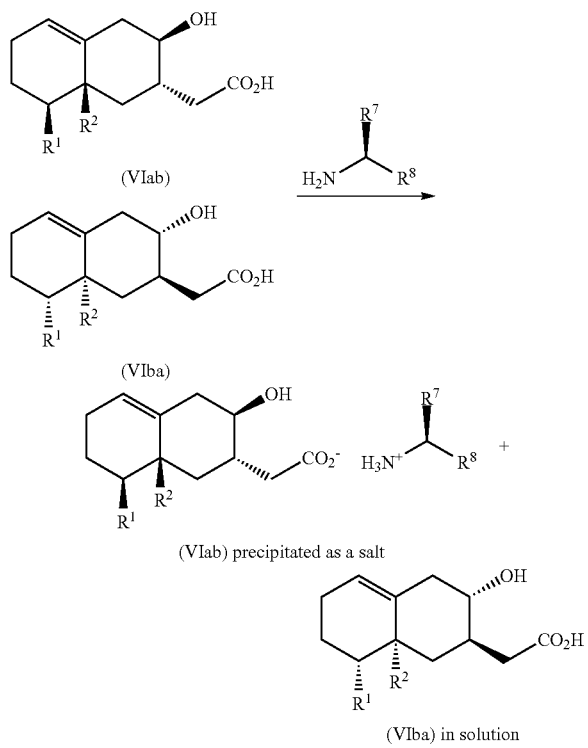

(VIab) precipitated as a salt (VIba) in solution wherein $R^1$ and $R^2$ are as defined above, preferably both methyl, and wherein $R^7$ and $R^8$ represent two different moieties such that the amine is a chiral amine.

A preferred chiral amine is α-methylbenzylamine (also referred to as (1)-phenylethylamine), although other similar amines in particular those that are commonly used for chiral resolution may also be applicable. α-Methylbenzylamine is preferred since it is easily available at relatively low cost and showed good results in the resolution.

A additional advantage of the resolution with the chiral amine, in particular with (S)-(−)α-methylbenzylamine or (R)-(+)-α-methylbenzylamine, is that any other diastereoisomers that may be formed during earlier synthetic steps can be separated from the desired enantiomer. Specifically, the inventors i.a. found that in case $R_1$ and $R_2$ are Me, small amounts (i.e. typically less than 10% mol/mol with respect to the desired diastereoisomer) of undesired diastereoisomers of compounds VII, Va, VIIIa, and VIa may be formed, and that these undesired diastereoisomers can be removed by using (S)-α-methylbenzylamine and/or (R)-α-methylbenzylamine.

Whether (S)-α-methylbenzylamine or (R)-α-methylbenzylamine results in the desired enantiomer of compound VIa can be determined by converting the acquired enantiomer to the compound of formula I (i.e. one specific enantiomer thereof) and comparing the residence time of the obtained product with the residence times of the racemic mixture of EPD. It was found that a chiral resolution of the compound of formula VIa with (S)-(−)-α-methylbenzylamine results in a salt that can lead to natural EPD. Vice-versa, a chiral resolution of the compound of formula VIa with (R)-(+)-α-methylbenzylamine results in a salt that can lead to the enantiomer of EPD.

Since the present method allows full control over the stereochemistry of all compounds described herein, the compound of formula I and the intermediate compounds according to formulae II, IIax, III, Va, VIa, and VIIIa can be obtained as mixture of enantiomers, or essentially enantiomerically pure since the method of the present invention enables the preparation of essentially enantiomerically pure compounds of formula VII and VIa (vide supra). Essentially enantiomerically pure means in the present context an enantiomeric ratio (er) of at least 90:10, preferably at least 95:5, more preferably at least 99:1 of the desired enantiomer with respect to the other enantiomer. Both enantiomers of the compounds according to formulae I, II, IIax, III, Va, VIa, and VIIIa can separately and essentially enantiomerically pure be obtained. Thus, yet another aspect of the present invention is essentially enantiomerically pure EPD analogue of formulae I, or intermediate compound of formulae II, IIax, III, Va, VIa or VIIIa having the absolute stereochemistry as indicated in formulae I, II, IIax, III, Va, VIa or VIIIa, or the opposite thereof.

EXAMPLES

The invention can be illustrated by the following non-limiting examples. The structures of all synthesized compounds were confirmed with nuclear magnetic resonance (NMR) spectroscopy.

Example 1 Synthesis of 4α-methyl-4,4a,5,6,7,8-hexahydronaphthalen-2(3H)-one

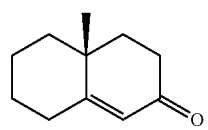

A solution of 2-methylcyclohexanone (52.26 g, 0.466 mol) and methyl vinyl ketone (68.28 g, 0.974 mol) in 850 mL dichloromethane was cooled, and technical benzenesulfonic acid (150.5 g, 0.952 mol) was added in portions over a 5 min period at −50 to −55° C. The magnetically stirred mixture was allowed to warm up, and placed in a mixture of ice and Dry Ice when it had reached −20° C. After overnight stirring, 300 mL water was added, followed by the slow addition of sodium bicarbonate (96 g, 1.142 mol). The mixture was stirred for 2 h, the layers were separated and the cloudy aqueous layer was extracted with 300 mL dichloromethane. Drying and rotary evaporation left a residue to which was added 700 mL heptane with swirling. After standing for 30 min, the supernatant was decanted from the residue, which was treated once more with 300 mL heptane. Rotary evaporation of the solution, followed by Kugelrohr distillation at 120-150° C./0.5 mbar gave 55.57 g (0.339 mol, 73%) of the product, which was pure enough for use in the next step.

Example 2 Synthesis of tert-butyl 2-((rel2R,8aR)-8α-methyl-3-oxo-1,2,3,5,6,7,8,8a-octahydronaphthalen-2-yl)acetate

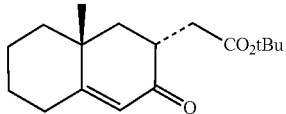 [SMILES: CC(C)(C)OC(=O)C[C@H]1C[C@@]2(C)CCCCC2=CC1=O]

An lithium diisopropylamide (LDA) solution was made by adding 2.5 N n-butyllithium in hexanes (56 mL, 140 mmol) to diisopropylamine (14.30 g, 141.6 mmol) in 45 mL tetrahydrofuran (THF) at <−20° C. The solution was cooled further and the ketone prepared above (13.92 g, 84.88 mmol), dissolved in 40 mL THF, was added over a 30 min period at <−60° C. The solution was stirred for 1 h at the same temperature, then a solution of t-butyl bromoacetate (27.95 g, 143.3 mmol) in 30 mL THF was added over a 45 min period at <−55° C. The mixture was stirred for 90 min, whereby the temperature rose to −17° C. It was then cooled to −50° C., and a solution of 26 g ammonium chloride in 100 mL water was added at once. Another 50 mL water was added, the layers were separated and the aqueous layer was extracted with 2×75 mL heptane. Drying and rotary evaporation gave a residue which was chromatographed on 115 g silica, starting with heptane as the eluent, and gradually increasing the polarity of the eluent by addition of toluene and ethyl acetate. The product fractions were combined to afford 16.33 g (58.74 mmol, 69%).

Example 3 Synthesis of tert-butyl 2-((rel2R,8aR)-3-acetoxy-8α-methyl-1,2,6,7,8,8a-hexahydronaphthalen-2-yl)acetate

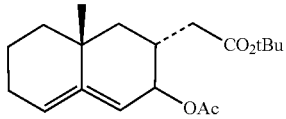

The ester of Example 2 (16.03 g, 57.66 mmol) was dissolved in 200 mL acetic anhydride. Sodium iodide (1.70 g, 11.3 mmol) was added, the mixture was cooled and chlorotrimethylsilane (38 mL, 297.3 mmol) was added over a 30 min period at −5 to 0° C. The mixture was stirred for 6 h, the last 2 h without cooling. The mixture was cooled again, and pyridine (46 mL, 0.569 mol) was added over a 20 min period at <−20° C. A rather thick, just stirrable suspension formed. Overnight stirring, followed by complete rotary evaporation at 60° C., gave a residue which was stirred with 100 mL ethyl acetate. Filtration, stirring with ethyl acetate, filtration, washing and rotary evaporation of the filtrate gave a residue, which was chromatographed on 95 g silica (pretreated with some pyridine) to yield 15.32 g of the dienol acetate (47.9 mmol, 83%).

Example 4 Synthesis of tert-butyl 2-((rel2R,3S,8aR)-3-hydroxy-8α-methyl-1,2,3,4,6,7,8,8a-octahydronaphthalen-2-yl)acetate

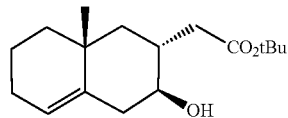 [SMILES: CC(C)(C)OC(=O)C[C@H]1C[C@@]2(C)CCCC=C2C[C@@H]1O]

A solution of the dienol acetate of Example 3 (15.32 g, 47.9 mmol) in 15 mL THF was cooled in ice, and 50 mL abs. ethanol was added. Sodium borohydride (3.80 g, 100 mmol) was added in portions at ca. −10° C. The mixture was stirred overnight, cooled in ice, and 60 mL ethyl acetate was added. The mixture was stirred for 10 min, 75 mL ice-cold water was added, the mixture was stirred for 10 min, 125 mL toluene was added, followed by the gradual addition of 25.2 g ammonium chloride. The mixture was stirred for an additional 30 min. the layers were separated and the organic layer was washed with 50 mL water. The successive aqueous layers were extracted with 100 mL toluene. The organic layers were dried and rotary evaporated to give 13.32 g of residue, which was used as such in the next step.

Example 5 Synthesis of 2-((rel2R,3S,8aR)-3-hydroxy-8α-methyl-1,2,3,4,6,7,8,8a-octahydronaphthalen-2-yl)acetic acid

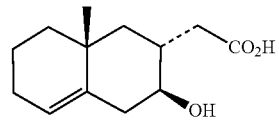 [SMILES: C[C@]12CCCC=C1C[C@H](O)[C@@H](CC(=O)O)C2]

The crude alcohol of Example 4 (13.05 g) was heated under reflux for 3 h with 100 mL ethanol, potassium hydroxide (10.1 g, 153.3 mmol), and 25 mL water. Most of the ethanol was subsequently removed by rotary evaporation. The residue was diluted with 50 mL water, then extracted with 150 mL toluene. The toluene layer was washed with 2×30 mL water. The combined aqueous layers were treated with 30 g citric acid, and then extracted with 150 and 100 mL toluene. Drying and rotary evaporation gave the crude acid (part of it already crystallized during the rotary evaporation), which was combined with another portion of crude acid (obtained from the reduction of 7.36 g dienol acetate and hydrolysis of the product). Chromatography on 85 g silica, successively using toluene, dichloromethane and TBME (this solvent dissolves the product and elutes it), gave the product which was recrystallized from toluene to yield 5.40 g of the desired hydroxy acid (it contains a small amount of another isomer; 24.1 mmol, 51% based on the dienol acetate). The filtrate contained 4.52 g of less pure hydroxy acid.

Example 6 Synthesis of (rel3aR,4aR,9aS)-4α-methyl-3a,4,4a,5,6,7,9,9a-octahydronaphtho[2,3-b]furan-2(3H)-one

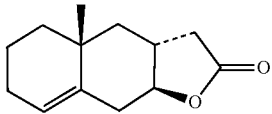

The hydroxy acid of Example 5 (5.20 g, 23.2 mmol) was mixed with 50 mL dichloromethane, and the solution was cooled in ice. 4-(N,N-dimethylamino)-pyridine (213 mg) and DCC (5.71 g, 27.67 mmol) were added, and the mixture was stirred overnight. The suspension was filtered, the solid being washed with dichloromethane. The filtrate was rotary evaporated and the residue was chromatographed on 50 g silica, using a gradient of ethyl acetate in heptane. The product fractions were combined with similar product fractions, obtained from lactonization of the less pure hydroxy acid of above. The total yield of the solidifying lactone was 4.54 g (22.04 mmol, 95%).

Example 7 Synthesis of (rel4aR,9aS)-4α-methyl-4a,5,6,7,9,9a-hexahydronaphtho[2,3-b]furan-2(4H)-one

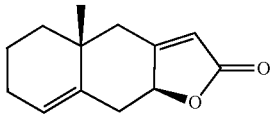

An LDA-solution was made from diisopropylamine (1.92 g, 19.0 mmol) in 15 mL THF, and n-butyllithium (7 mL, 2.5 N in hexanes, 17.5 mmol) at <−15° C. The lactone of Example 6 (2.10 g, 10.19 mmol), dissolved in 10 mL THF, was added over a 10 min period at <−65° C. The addition funnel was rinsed with 10 mL THF. The solution was stirred for 45 min at <−70° C. Phenylselenyl bromide (4.02 g, 16.7 mmol), dissolved in 15 mL THF, was added over a 10 min period at <−65° C. The mixture was stirred for 3¾ h, whereby the temperature rose to 10° C. The mixture was poured into a solution of 6 g citric acid in 40 mL water. Extraction was performed with 75 and 50 mL toluene. The successive organic layers were washed with 30 mL water, then dried and rotary evaporated, leaving 4.83 g of residue.

This residue was dissolved in 50 mL THF. Acetic acid (660 mg, 11 mmol) was added, and the solution was cooled in ice. Hydrogen peroxide (5.52 g of a 35% solution, 47.0 mmol) was added in a few minutes, and the mixture was stirred for 31 h, whereby the temperature rose to ca. 12° C. A mixture of 10 g sodium bicarbonate and 40 mL water was added, and the mixture was stirred for 1 h. Extraction was performed with 2×75 mL toluene. The successive organic layers were washed with 25 mL water, then dried and rotary evaporated. The residue was chromatographed on 45 g silica, using a gradient of ethyl acetate in heptane. This gave 654 mg of the unsaturated lactone (3.20 mmol, 31%).

Example 8 Synthesis of (rel3aS,4aR,9aS)-4α-methyl-3a,4,4a,5,6,7,9,9a-octahydronaphtho[2,3-b]furan-2(3H)-one

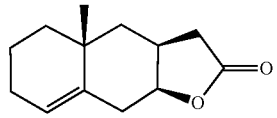

Nickel chloride hexahydrate (193 mg, 0.81 mmol) was added to a solution of the unsaturated lactone of Example 7 (654 mg, 3.20 mmol) in 45 mL methanol. The mixture was cooled, and sodium borohydride (384 mg, 10 mmol) was added at −45° C. The mixture was stirred for 2½ h at −27 to −32° C., then it was poured into a mixture of 90 mL toluene and 80 mL cold 2 N hydrochloric acid. The mixture was shaken for a few minutes, the layers were separated, and the organic layer was washed with 5 g sodium bicarbonate in 25 mL water. The successive aqueous layers were extracted with 2×40 mL toluene, and the organic layers were dried and rotary evaporated. The residue was chromatographed on 20 g silica, using a gradient of ethyl acetate in heptane. This gave 260 mg of the saturated lactone, which crystallized on standing (1.26 mmol, 39%).

Example 9 Synthesis of (rel3aS,4aR,9aS)-4α-methyl-3-methylene-3a,4,4a,5,6,7,9,9a-octahydronaphtho[2,3-b]furan-2(3H)-one (mono methyl analogue)

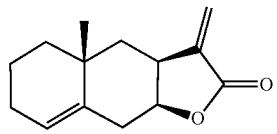 [SMILES: C=C1C(=O)O[C@H]2CC3=CCCC[C@]3(C)C[C@@H]12]

The lactone of Example 8 (260 mg, 1.26 mmol) was mixed with ethyl formate (280 mg, 3.78 mmol) and 5 mL THF. The solution was added over a 30 min period to 1 N t-BuOK in THF (1.65 mL, 1.65 mmol), with ice-cooling. The dropping funnel was flushed with 5 mL THF. The mixture was stirred overnight, then warmed for 2½h at 45° C., then cooled in ice. Paraformaldehyde (98 mg, 3.27 mmol) was added, the mixture was stirred for 30 min at rt, then warmed for 1½ h at 55° C. The mixture was cooled, and 50 mL t-butylmethyl ether (TBME) was added, followed by 2 g potassium carbonate in 25 mL water. After stirring for 10 min, the layers were separated, and the aqueous layer was extracted with 30 mL TBME. The successive organic layers were washed with 15 mL water, then dried and rotary evaporated. The residue consisted of essentially pure methylene lactone (220 mg, 1.01 mmol, 80%).

Figure 6:
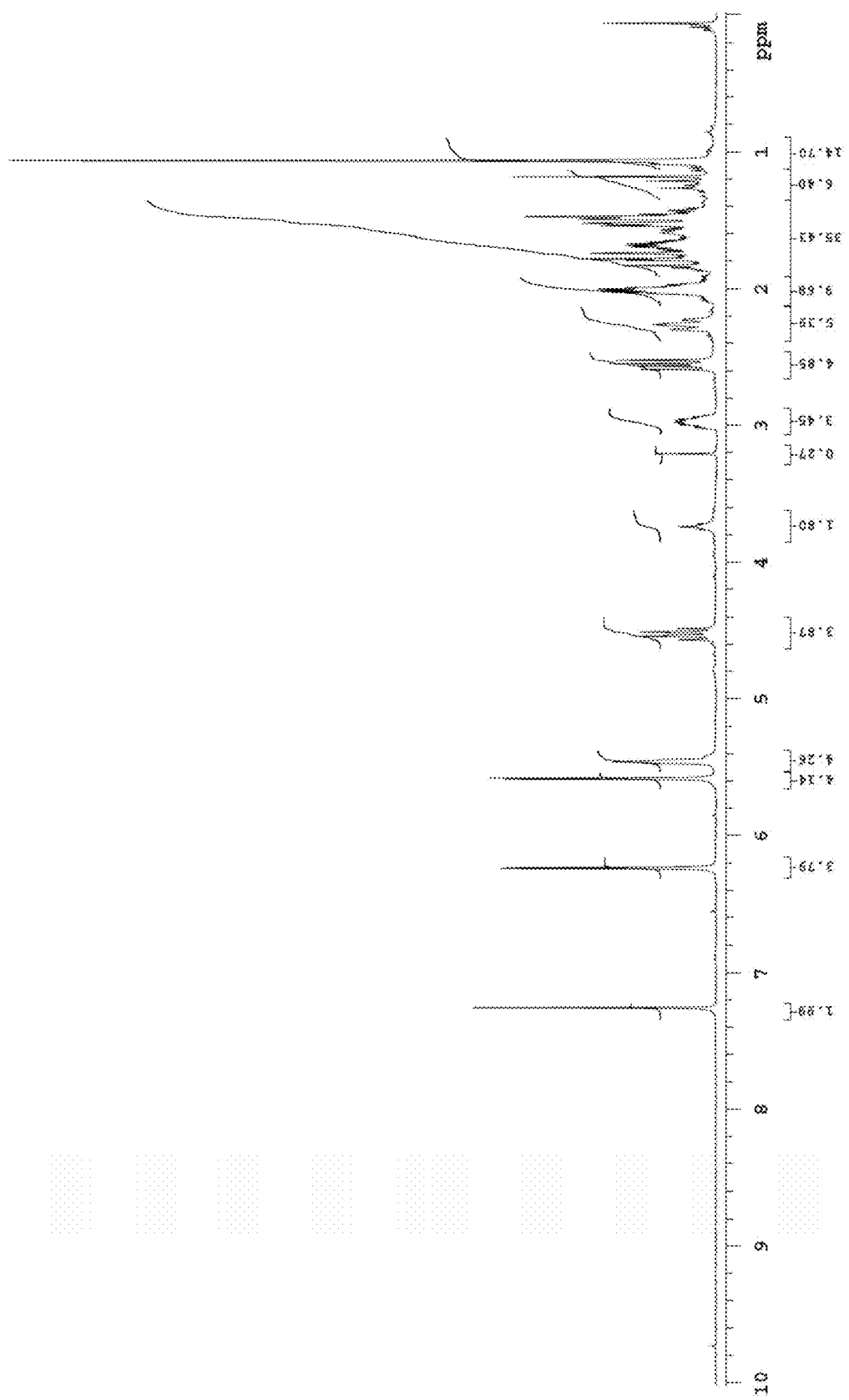
FIG. 6 shows H-NMR spectrum of the racemic mixture of the monomethyl analogue in accordance with the present invention.

FIG. 6 shows H-NMR spectrum of the racemic mixture of the monomethyl analogue in accordance with the present invention.

Example 10 Synthesis of (rel4aS,5R)-4a,5-dimethyl-4,4a,5,6,7,8-hexahydronaphthalen-2(3H)-one

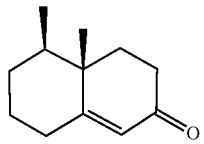

A solution of 2,3-dimethylcyclohexanone (42.90 g, 0.340 mol) and methyl vinyl ketone (50.1 g, 0.715 mol) in 600 mL dichloromethane was cooled, and technical benzenesulfonic acid (112.4 g, 0.710 mol) was added in 3 portions over a 5 min period at <−55° C. The magnetically stirred mixture was allowed to warm up, and placed in a mixture of ice and Dry Ice when it had reached −17° C. After overnight stirring, 300 mL cold water was added, followed by the slow addition of sodium bicarbonate (80 g, 0.95 mol). The mixture was stirred for another 30 min, the layers were separated and the aqueous layer was extracted with 250 mL dichloromethane. The successive organic layers were washed with 100 mL water. Drying and rotary evaporation left a residue to which was added 500 mL heptane with swirling. After standing for 1 h, the supernatant was decanted from the residue, which was treated once more with 300 mL heptane. Rotary evaporation of the solution, followed by Kugelrohr distillation at 120-150° C./0.5 mbar gave 29.35 g (0.165 mol, 48%) of the product, which was pure enough for use in the next step.

Example 11 Synthesis of tert-butyl 2-((rel2R,8R,8aS)-8,8a-dimethyl-3-oxo-1,2,3,5,6,7,8,8a-octahydronaphthalen-2-yl)acetate

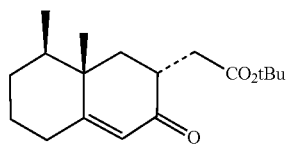 [SMILES: C[C@@H]1CCCC2=CC(=O)[C@@H](CC(=O)OC(C)(C)C)C[C@]21C]

An LDA solution was made by adding 2.5 N n-butyllithium in hexanes (56 mL, 140 mmol) over a 15 min period to diisopropylamine (14.68 g, 145.3 mmol) in 50 mL THF at <−30° C. The solution was cooled further and the ketone of Example 10 (15.15 g, 85.1 mmol), dissolved in 45 mL THF, was added over a 30 min period at <−65° C. The solution was stirred for 1 h at the same temperature, then a solution of t-butyl bromoacetate (29.0 g, 148.7 mmol) in 30 mL THF was added over a 45 min period at <−60° C. The mixture was stirred for 3 h, whereby the temperature rose to −15° C. It was then cooled to −50° C., and a solution of 26 g ammonium chloride in 100 mL water was added at once. Another 50 mL water was added, the layers were separated and the aqueous layer was extracted with 2×75 mL heptane. Drying and rotary evaporation gave a residue which was chromatographed on 115 g silica, starting with heptane as the eluent, and gradually increasing the polarity of the eluent by addition of toluene and ethyl acetate. The product fractions were combined to afford 13.86 g (47.47 mmol, 56%).

Example 12 Synthesis of tert-butyl 2-((rel2R,8R,8aS)-3-acetoxy-8,8a-dimethyl-1,2,6,7,8,8a-hexahydronaphthalen-2-yl)acetate

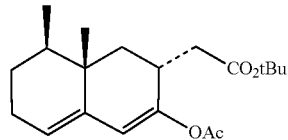 [SMILES: CC(=O)OC1=CC2=CCC[C@@H](C)[C@]2(C)C[C@@H]1CC(=O)OC(C)(C)C]

The ester of Example 11 (13.66 g, 46.78 mmol) was dissolved in 200 mL acetic anhydride. Sodium iodide (1.50 g, 10 mmol) was added, the mixture was cooled and chlorotrimethylsilane (35 mL, 274 mmol) was added over a 20 min period at −10 to −20° C. The mixture was stirred for 6 h, the last 3 h at rt. The mixture was cooled again, and pyridine (44 mL, 0.544 mol) was added over a 20 min period at −5 to −15° C. A rather thick, just stirrable suspension formed. Overnight stirring, followed by complete rotary evaporation at 60° C., gave a residue which was stirred with 150 mL ethyl acetate for a few hours. Filtration, washing and rotary evaporation of the filtrate gave a residue, which was chromatographed on 90 g silica (pretreated with some pyridine) to yield 13.77 g of the dienol acetate (41.22 mmol, 88%).

Example 13 Synthesis of tert-butyl 2-((rel2R,3S,8R,8aS)-3-hydroxy-8,8a-dimethyl-1,2,3,4,6,7,8,8a-octahydronaphthalen-2-yl)acetate

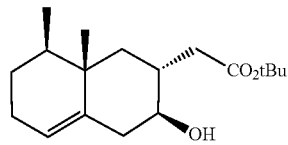 [SMILES: C[C@@H]1CCC=C2C[C@H](O)[C@@H](CC(=O)OC(C)(C)C)C[C@]21C]

A solution of the dienol acetate of Example 12 (13.77 g, 41.22 mmol) in 15 mL THF was cooled in ice, and 50 mL abs. ethanol was added. Sodium borohydride (3.28 g, 86.3 mmol) was added in portions at ca. −10° C. The mixture was stirred overnight, cooled in ice, and 50 mL ethyl acetate was added. The mixture was stirred for 10 min, 75 mL ice-cold water was added, the mixture was stirred for 10 min, 75 mL toluene was added, followed by the gradual addition of 20 g ammonium chloride. The mixture was stirred for an additional 45 min. 25 mL water and 100 mL toluene were added, the layers were separated and the organic layer was washed with 50 mL water. The successive aqueous layers were extracted with 150 mL toluene. The organic layers were dried and rotary evaporated to give 13.20 g of residue, which was used as such in the next step.

Example 13 Synthesis of 2-((rel2R,3S,8R,8aS)-3-hydroxy-8,8a-dimethyl-1,2,3,4,6,7,8,8a-octahydronaphthalen-2-yl)acetic acid

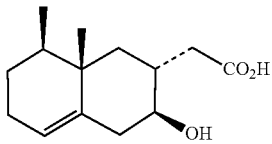 [SMILES: C[C@@H]1CCC=C2C[C@H](O)[C@@H](CC(=O)O)C[C@]21C]

The crude alcohol of Example 12 (12.96 g) was heated under reflux for 2 h with 100 mL ethanol, potassium hydroxide (9.54 g, 144.8 mmol), and 25 mL water. Another 25 mL water was added and the mixture was stirred at rt for the weekend, then heated under reflux for 1 h. Most of the ethanol was subsequently removed by rotary evaporation. The residue was diluted with 50 mL water, then extracted with 200 mL TBME. The organic layer was washed with 2×30 mL water (it contained a small amount of the diol, due to reduction of the ester in the previous step). The combined aqueous layers were treated with 30 g citric acid, and then extracted with 3×100 mL TBME. Drying and rotary evaporation gave the crude acid, to which 40 mL toluene was added. 20 mL heptane was added with stirring, and the suspension was stirred overnight. Filtration and washing with toluene/heptane 1/1 gave 4.54 g of the hydroxy acid (19.0 mmol, 47%, based on the dienol acetate). The filtrate contained another 4.33 g impure hydroxy acid.

Example 14 Synthesis of (rel3aR,4aS,5R,9aS)-4a,5-dimethyl-3a,4,4a,5,6,7,9,9a-octahydronaphtho[2,3-b]furan-2(3H)-one

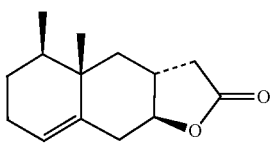

A suspension of hydroxy acid of Example 13 (4.33 g, 18.2 mmol) and 4-(N,N-dimethylamino)-pyridine (150 mg) in 50 mL dichloromethane (DCM) was cooled in ice. Dicyclohexylcarbodiimide (4.50 g, 21.8 mmol) was added and after 10 min the ice bath was removed and the mixture was stirred at room temperature overnight. The suspension was diluted with 20 mL TBME and filtered. The solid was washed with 50 mL DCM. The filtrate was concentrated to an oily residue of 5.3 g, which was chromatographed on 100 g silica, using 10% ethyl acetate in heptanes. The product fractions were concentrated to give 2.2 g of the lactone as a white solid (yield 55%).

The impure fractions were combined with the product of another lactonization reaction performed with 4.33 g of impure hydroxy acid and again chromatographed on 100 g silica. This afforded 0.6 g of impure lactone as yellow oil which solidified on standing.

A 100 mg sample of the white solid was crystallized from 10 mL heptanes, which afforded 30 mg of crystalline solid.

Example 15 Synthesis of (rel4aS,5R,9aS)-4a,5-dimethyl-4a,5,6,7,9,9a-hexahydronaphtho[2,3-b]furan-2(4)-one

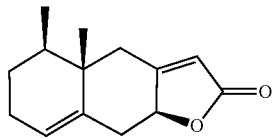 [SMILES: C[C@@H]1CCC=C2C[C@@H]3OC(=O)C=C3C[C@]21C]

An LDA-solution was made from diisopropylamine (0.82 g, 8 mmol) in 20 mL THF, and n-butyllithium (2 mL, 2.5 N in hexanes, 5 mmol) at <0° C. After 10 min the solution was cooled to −70° C. and the lactone of Example 14 (0.66 g, 3 mmol), dissolved in 10 mL THF, was added over a 1 min period at <−65° C. The solution was stirred for 30 min at <−70° C. Carbon tetrabromide (1.32 g, 4 mmol), dissolved in 10 mL THF, was added over a 10 min period at <−65° C. The mixture, which turned dark-yellow to orange, was stirred for 4 h at <−65° C. The cold mixture was poured into a solution of 15 g ammonium chloride in 100 mL water. The mixture was extracted with 3×50 mL TBME. The combined organic layers were washed with 20 mL brine, then dried on sodium sulfate and rotary evaporated to a residue consisting of mainly alpha-bromolactone.

This residue was dissolved in 10 mL DMF. 1,8-diazabicyclo[5.4.0]undec-7-ene (0.6 g, 4 mmol) was added, and the solution was stirred at room temperature overnight. The solution was diluted with 50 mL TBME and successively washed with 20 mL 0.5 N hydrochloric acid, 20 mL water, 20 mL brine, and then dried on sodium sulfate and rotary evaporated. The residue was chromatographed on 24 g silica, using a gradient of 0 to 20% ethyl acetate in heptane (ISCO). This afforded 310 mg of the unsaturated lactone as an oil that solidified on standing (47% yield).

Example 16 Synthesis of (rel3aS,4aS,5R,9aS)-4a,5-dimethyl-3a,4,4a,5,6,7,9,9a-octahydronaphtho[2,3-b]furan-2(3)-one

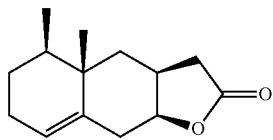 [SMILES: C[C@@H]1CCC=C2C[C@@H]3OC(=O)C[C@@H]3C[C@]21C]

Nickel chloride hexahydrate (60 mg, 0.25 mmol) was added to a solution of the unsaturated lactone of Example 15 (220 mg, 1 mmol) in 20 mL methanol. The mixture was cooled to −40° C., and sodium borohydride (115 mg, 3 mmol) was added at −40° C. The mixture was stirred for 3 h at −35 to −25° C., then it was poured into a mixture of 50 mL TBME and 10 mL 1 N hydrochloric acid. The mixture was shaken for a few minutes, the layers were separated, and the water layer was extracted with 20 mL TBME. The combined organic layer was washed with 25 mL of saturated aqueous sodium bicarbonate, then dried on sodium sulfate and concentrated to give 160 mg of the saturated lactone as an off-white solid (73%).

Example 17 Synthesis of (rel3aS,4aS,5R,9aS)-4a,5-dimethyl-3-methylene-3a,4,4a,5,6,7,9,9a-octahydronaphtho[2,3-b]furan-2(3H)-one

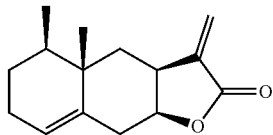 [SMILES: C=C1C(=O)O[C@H]2CC3=CCC[C@@H](C)[C@]3(C)C[C@@H]12]

The lactone of Example 16 (160 mg, 0.72 mmol) was mixed with ethyl formate (160 mg, 2.16 mmol) and 5 mL THF. This solution was added over a 15 min period to 1 N t-BuOK in THF (1.0 mL, 1.0 mmol), with ice-cooling. The mixture was stirred at room temperature overnight, then warmed for 2 h at 50° C., and then cooled in ice. Paraformaldehyde (66 mg, 2 mmol) was added, and the mixture was warmed for 2 h at 50° C. The mixture was cooled to room temperature, and 25 mL TBME was added, followed by 1 g potassium carbonate in 15 mL water. After stirring for 30 min, the layers were separated, and the aqueous layer was extracted with 25 mL TBME. The combined organic layers were washed with 15 mL water, then with 15 mL brine, then dried on sodium sulfate and rotary evaporated to give 150 mg of methylene lactone as colorless oil (90% yield). Besides the presence of 5 to 10% of an impurity, the NMR was identical to a sample of EPD. HPLC-MS shows a peak at 2.0 min. (95% at 215 nm) with m/z 233 (M+1).

35 mg of the material was used for separation of the enantiomers with chiral preparative HPLC (type Chiralpak IC (250×20 mm×5 μm) using a 9:1 mixture of heptane and isopropyl alcohol as eluent). A spiking experiment with an authentic sample of EPD showed that the second eluting peak was identical to EPD.

Figure 2:
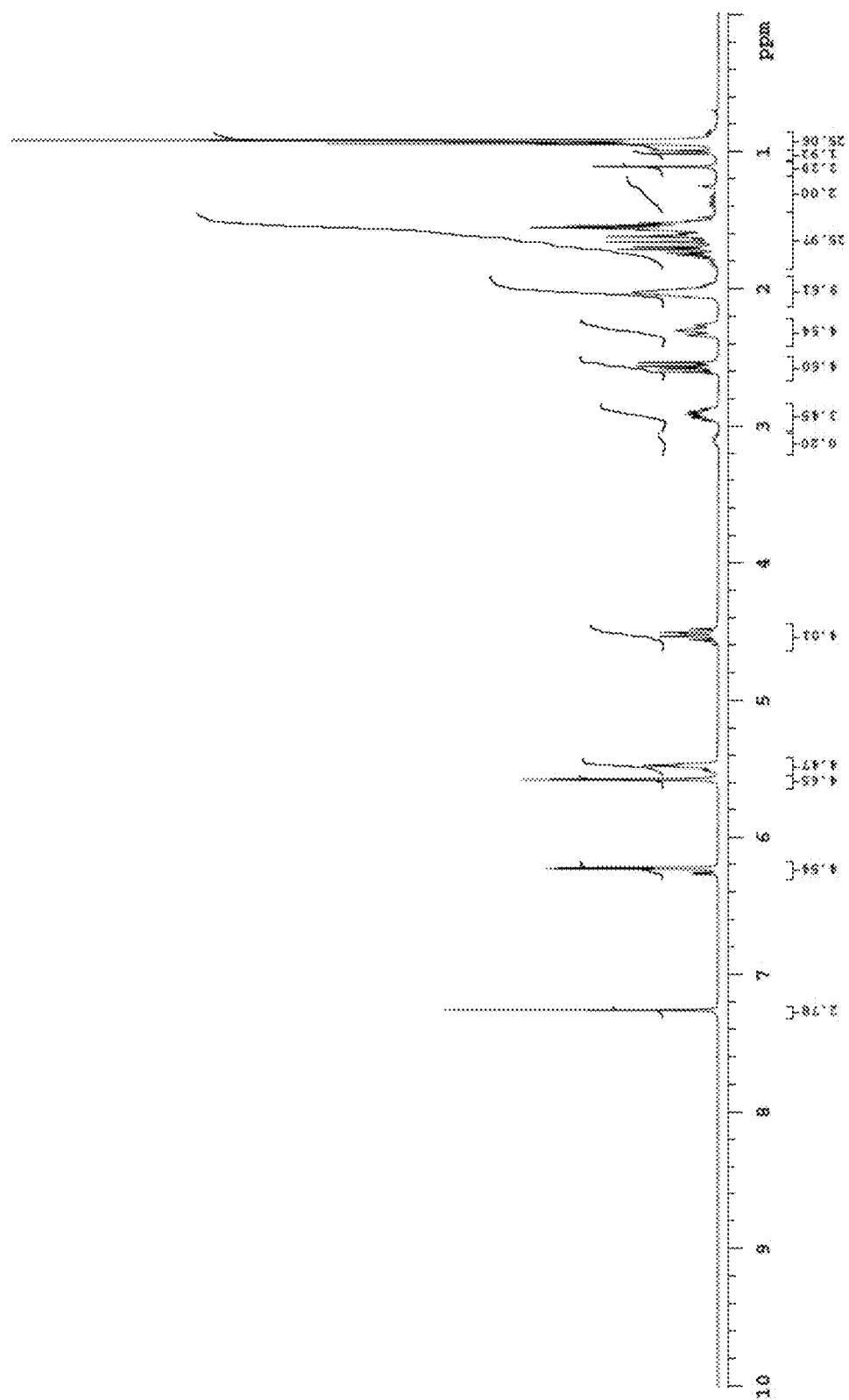
FIG. 2 shows the H-NMR spectrum of the racemic mixture comprising EPD and its enantiomer in accordance with the present invention.

FIG. 2 shows the H-NMR spectrum of the racemic mixture comprising EPD and its enantiomer in accordance with the present invention.

Figure 3:
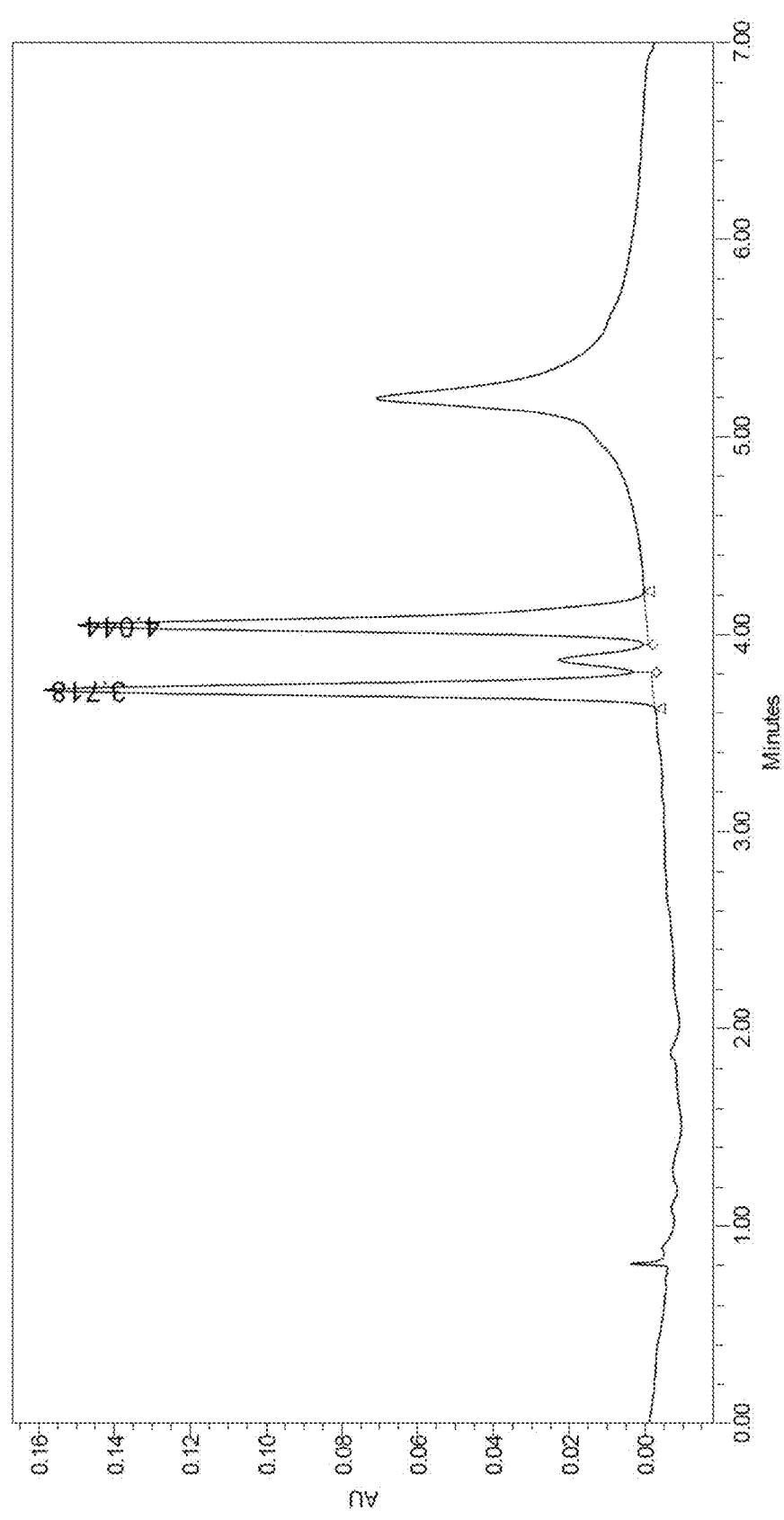
FIG. 3 shows the HPLC chromatogram of the racemic mixture comprising EPD and its enantiomer in accordance with the present invention.

FIG. 3 shows the HPLC chromatogram of the racemic mixture comprising EPD and its enantiomer in accordance with the present invention. The HPLC chromatograph was obtained with a Waters Acquity UPC$^2$ system with PDA detector and QDA mass detector, including a phenomenex lux amylose-2 (3.0×150 mm; 3 μm) column with $CO_2$ and methanol as mobile phases.

Figure 4:
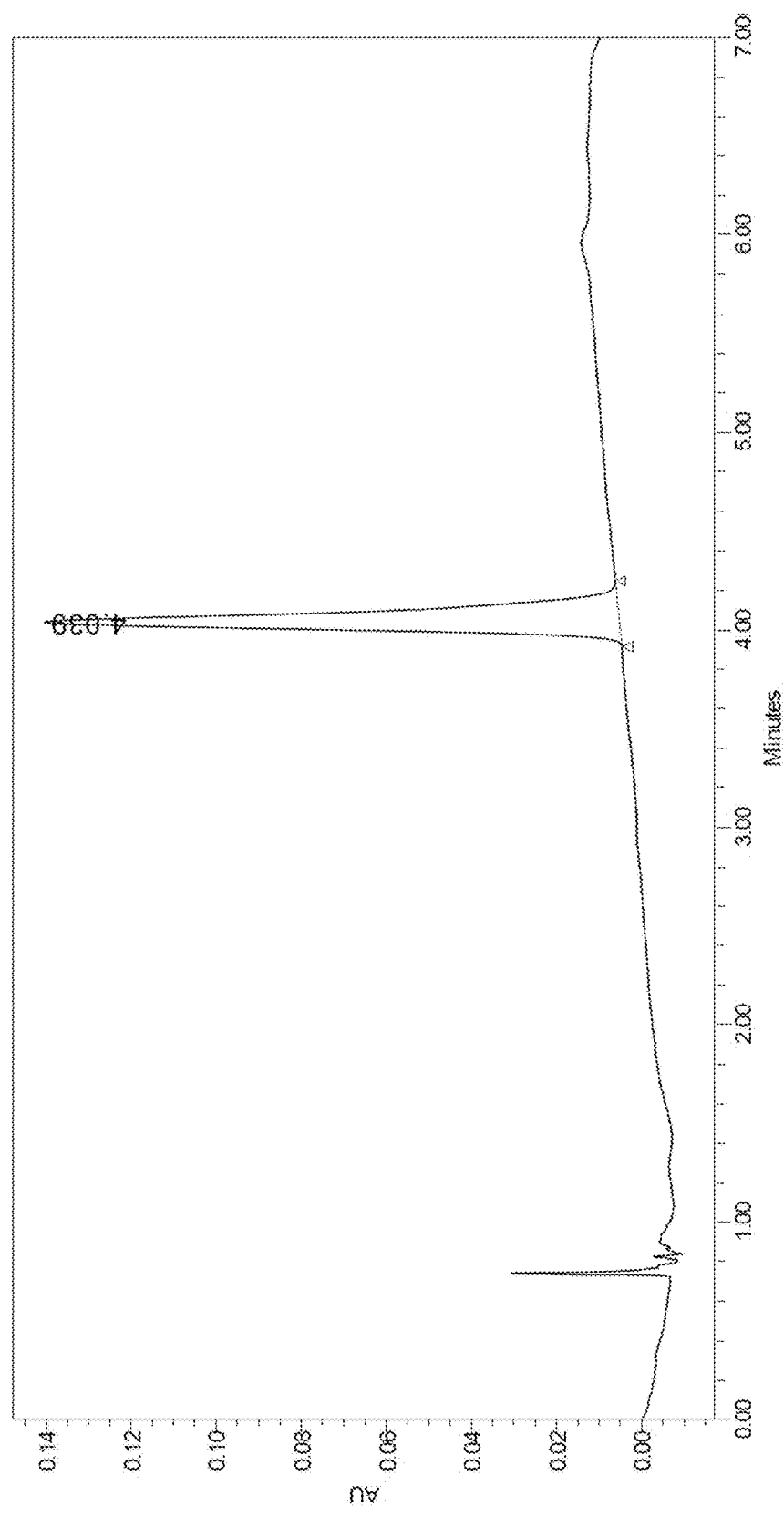
FIG. 4 shows the HPLC chromatogram of EPD as prepared in accordance with the present invention.

FIG. 4 shows the HPLC chromatogram (obtained as described above for FIG. 3) of EPD as prepared in accordance with the present invention.

Figure 5:
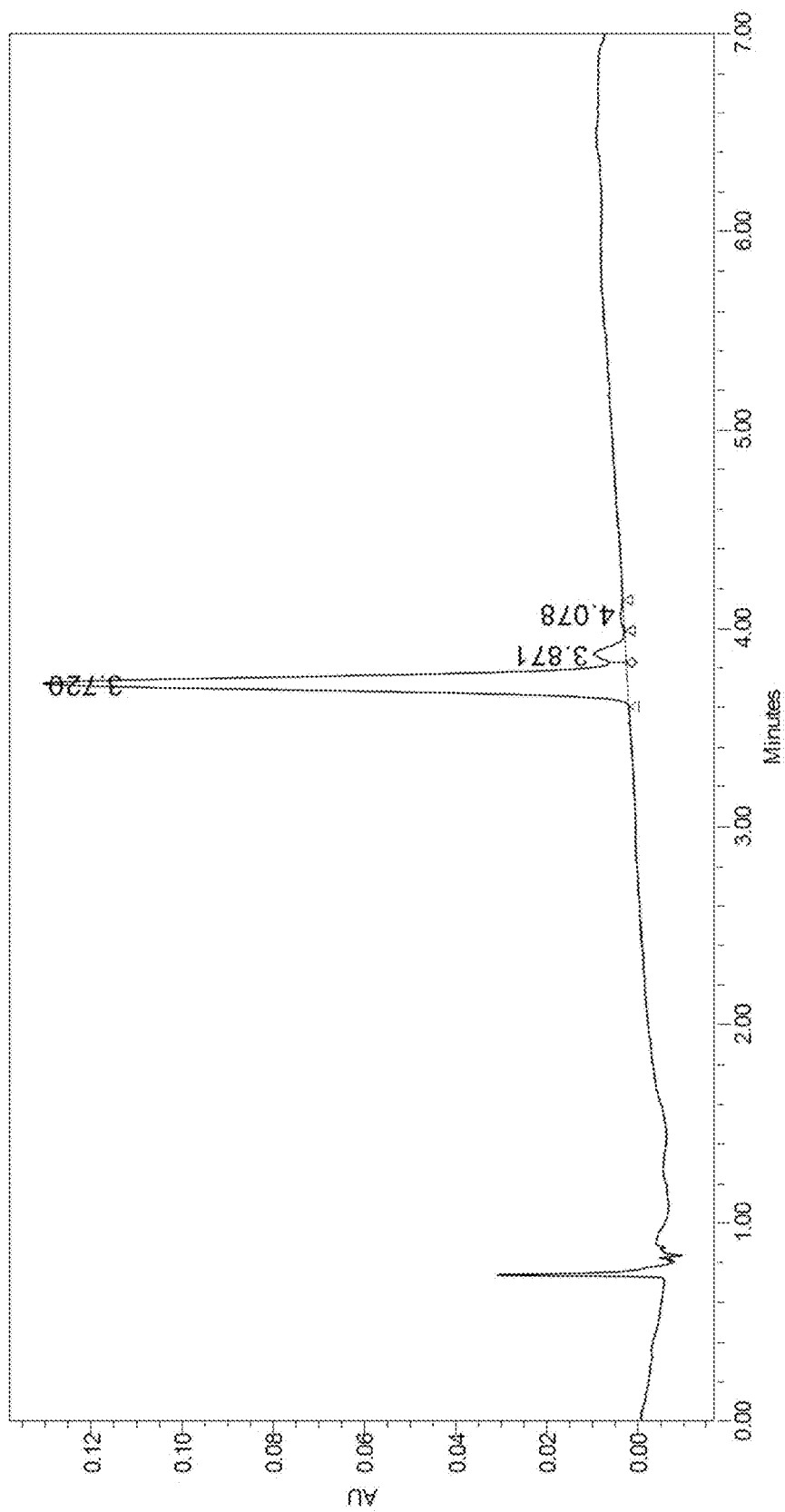
FIG. 5 shows the HPLC chromatogram of the enantiomer of EPD as prepared in accordance with the present invention.

FIG. 5 shows the HPLC chromatogram (obtained as described above for FIG. 3) of the enantiomer of EPD as prepared in accordance with the present invention.

Example 18 Synthesis of (rel4aR,9aS)-4α-methyl-4a,5,6,7,9,9a-hexahydronaphtho[2,3-b]furan-2(4H)-one—Bromination of Lactone with Carbon Tetrabromide as Alternative for Phenylselenyl Bromide

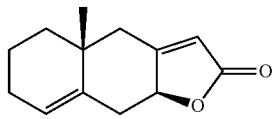

An LDA-solution was made from diisopropylamine (0.41 g, 4.0 mmol) in 10 mL THF, and n-butyllithium (1 mL, 2.5 N in hexanes, 2.5 mmol) at <–0° C. The lactone of Example 6 (0.31 g, 1.5 mmol), dissolved in 5 mL THF, was added over a 5 min period at <–65° C. The solution was stirred for 30 min at <–70° C. Carbon tetrabromide (0.66 g, 2 mmol), dissolved in 10 mL THF, was added over a 10 min period at <–65° C. The mixture, which turned dark-yellow to orange, was stirred for 4 h at <–60° C. The cold mixture was poured into a solution of 7.5 g ammonium chloride in 50 mL water. The mixture was allowed to reach room temperature and then extracted with 3×50 mL TBME. The combined organic layers were washed with 20 mL brine, then dried on sodium sulfate and rotary evaporated to 0.67 g of an oil residue consisting of mainly alpha-bromolactone.

This residue was dissolved in 5 mL DMF. 1,8-Diazabicyclo[5.4.0]undec-7-ene (0.23 g, 1.5 mmol) was added, and the solution was stirred at room temperature overnight. The solution was diluted with 50 mL TBME and successively washed with 20 mL 0.5 N hydrochloric acid, 3×20 mL water, 20 mL brine, and then dried on sodium sulfate and rotary evaporated. The residue was chromatographed on 24 g silica, using a gradient of 0 to 20% ethyl acetate in heptane (ISCO). This afforded 100 mg of the unsaturated lactone as an oil (33% yield).

Example 19 In Vitro Activity of Synthesized Compounds

The following solutions in DMSO were prepared:
Solution 3: synthetic EPD (5.24 μg/ml);
Solution 4: synthetic enantiomer of EPD (4.94 μg/ml);
Solution 5: racemic mixture of methyl analogue (6.8 μg/ml);
Solution EPD: natural EPD (i.e. isolated from *Calomeria amaranthoides* as described in Duke, Van Haaften, & Tran, 2011 Green Sustainable Chem Vol 1:123-7).) (4.7 μg/ml).

The cytotoxic activity of the compounds was tested using methods as described earlier (van Haaften et al. Journal of Experimental & Clinical Cancer Research (2015) 34:38). In short, 3×10$^4$ cells of the ovarian cancer cell line JC (Van Haaften-Day et al. Cancer Res. 1983) were seeded in 24-well plates (Costar, Denmark) in DMEM/F12 medium (Invitrogen) containing 10% of Fetal Calf Serum (FCS, Sigma), 50 U penicillin and 50 μg/mL streptomycin (Invitrogen). The cells were incubated at 37° C. in a 9% $CO_2$ incubator with 95% humidity. After 24 hours, solutions 1-6 were added to the cell cultures.

Cytotoxic activity of each of the compounds was determined after 72 hours in a standard Presto blue assay (see Van Haaften et al. J Exp Clin Cancer Res. 2015 34(1): 38 for details on the method). Each compound's solution as described above was diluted 100, 200 and 400 times respectively.

The results are depicted in FIG. 1A. Solutions 3 (synthetic EPD) and 4 (synthetic enantiomer of EPD) demonstrate similar or even stronger cytotoxic activity than natural EPD isolated from *Calomeria amaranthoides*. Solution 5, the racemic mixture of the (mono) methyl analogue, also demonstrates cytotoxic activity.

Figure 1B:
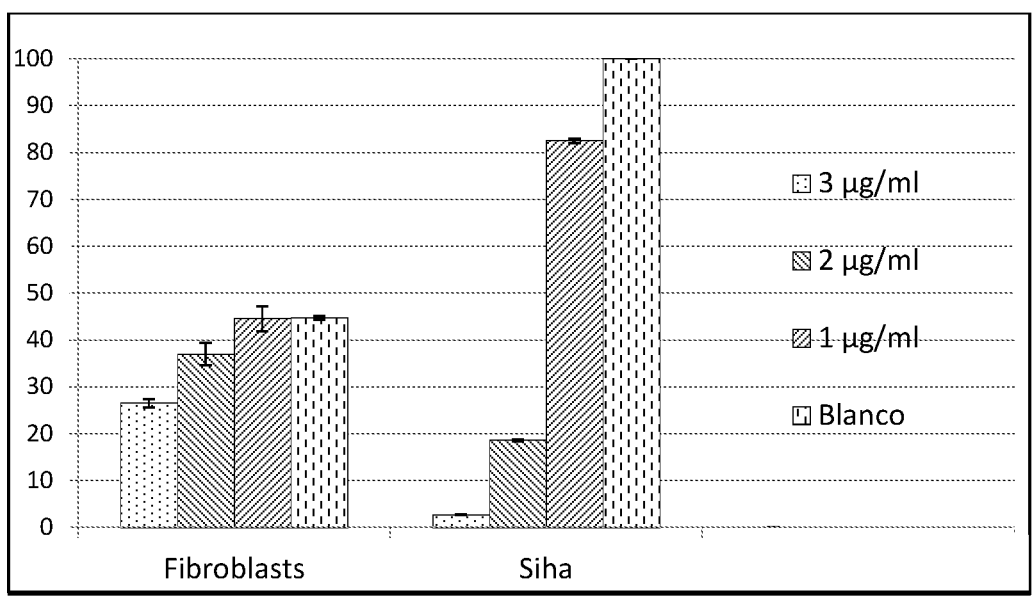

Further, the effect of synthetic EPD (1-3 μg/mL) was studied on normal fibroblasts and compared with the effect on a cervical cancer cell line Siha (FIG. 1B). The results indicated that the dose-dependent effect was much higher on cancer cells than on fibroblasts. At a concentration of 1 μg/mL, fibroblast growth was unaffected, whereas cancer cell growth was reduced by almost 20%. At a concentration of 2 g/mL, fibroblast growth was reduced by almost 20%, whereas cancer cell growth was reduced by more than 80%, and at a concentration of 3 μg/mL, fibroblast growth was reduced by 35%, whereas cancer cell growth was reduced by almost 97%.

Figure 1C:
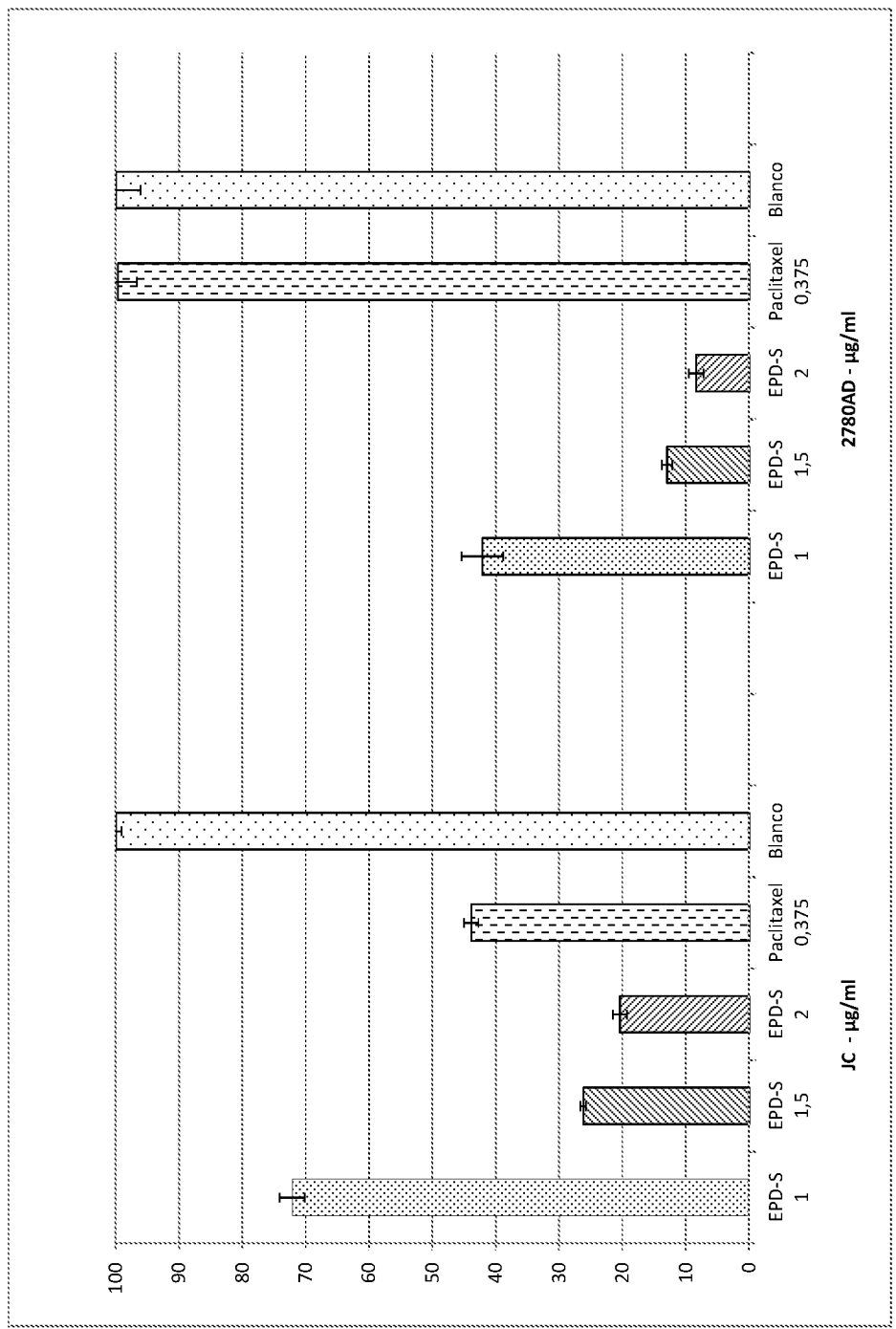

Also the effect of synthetic EPD was tested on an ovarian cancer cell line A2780AD, ATCC using methods as described above, whereby the experiment was ended after 72 hrs. Cell line A2780AD, a multi-drug resistant human ovarian cancer cell line, is resistant to paclitaxel. It was shown that at 1, 1.5 and 2 μg/mL of synthetic EPD, the growth of the cell line after 72 hrs was reduced to 40%, 13% and 8% of the control value (100%, medium), respectively. Indeed, full resistance to 0.375 μg/mL of paclitaxel was observed in cell line A2780AD. Using the ovarian cancer cell line JC as a control, it was observed that synthetic EPD was at least as effective as paclitaxel in inhibiting these cells (FIG. 1C).

Example 20 Resolution of 2-((rel2R,3S,8R,8aS)-3-hydroxy-8,8a-dimethyl-1,2,3,4,6,7,8,8a-octahydronaphthalen-2-yl)acetic acid (rel4aS,5R)-4a,5-dimethyl-4,4a,5,6,7,8-hexahydronaphthalen-2(3H)-one (14.45 g, 81.18 mmol) was converted in a number of steps into crude 2-((rel2R,3S,8R,8aS)-3-hydroxy-8,8a-dimethyl-1,2,3,4,6,7,8,8a-octahydronaphthalen-2-yl)acetic acid, as described above. This crude acid (mixture of enantiomers) was dissolved in 75 mL isopropanol and then (S)-(−)-methylbenzylamine ((S)-(−)-MBA, 8.60 g, 71.0 mmol) was added. The mixture was stirred for 3 d and then filtered, the solid being washed with 30 mL isopropanol—THF (2/1). A yield of 1.96 g of the (S)-(−)-MBA-salt of a single enantiomer of 2-((rel2R,3S,8R,8aS)-3-hydroxy-8,8a-dimethyl-1,2,3,4,6,7,8,8a-octahydronaphthalen-2-yl) acetic acid (herein also referred to as the (S)-(−)-MBA-salt) was obtained. Chiral HPLC indicated that the acid had an enantiomeric excess (ee) of 80-90% (er of 90:10 to 95:5) and that it was contaminated with a small amount of another enantiomer.

Figure 7:
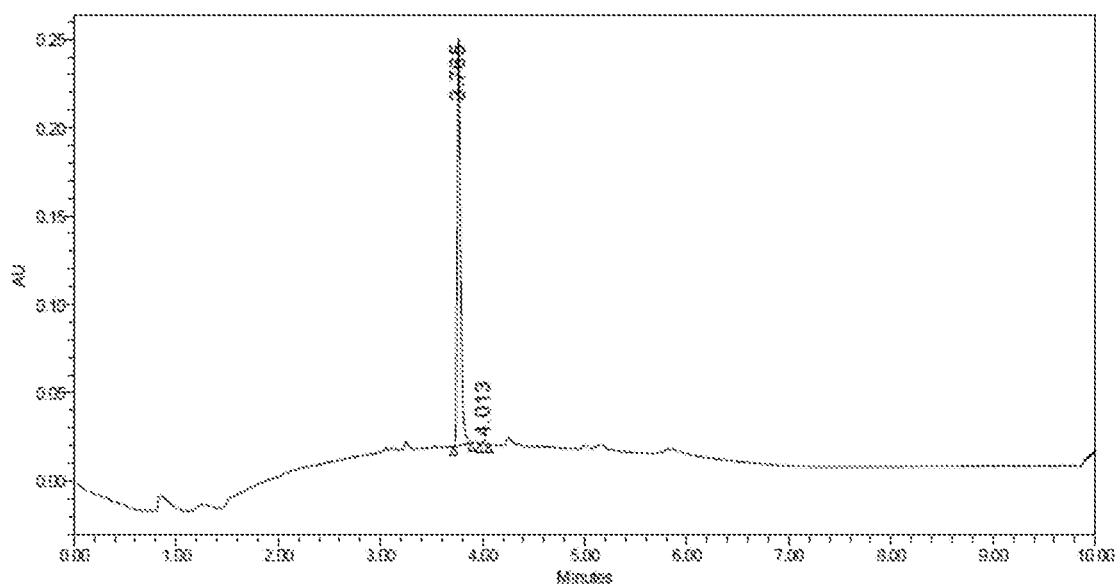
FIG. 7 shows the HPLC chromatogram of enantiomerically pure VIa.

The filtrate obtained in the previous filtration step was rotary evaporated and the residue was stirred with 150 mL TBME and 45 mL 10% sodium hydroxide solution. The layers were separated and the organic layer was washed with 30 and 20 mL water. The successive aqueous layers were extracted with 100 mL TBME. The combined aqueous layers were acidified with 20.5 g citric acid, and then extracted with 2×125 mL TBME. Drying and rotary evaporation gave 10 g residue which was dissolved in 40 mL isopropanol. (R)-(+)-methylbenzylamine (5.38 g, 44.4 mmol) was added, resulting in a thick suspension. 20 mL isopropanol was added and the mixture was stirred overnight. Filtration, washing with 40 mL isopropanol—THF (2/1) and air-drying gave 2.07 g of the (R)-(+)-MBA-salt salt of the other enantiomer as that was obtained with (S)-(−)-MBA. Chiral HPLC indicated that this enantiomer was obtained with an ee of >97% (i.e. er of >98:2, cf. FIG. 7).

The filtrate obtained in the previous filtration step was rotary evaporated and the acid was liberated from it, as described above. It was then chromatographed on 70 g silica using dichloromethane and then dichloromethane-methanol as the eluent. The cis-lactone (from the acid with the OH pointed downward, cf. the structure in Example 14; this acid lactonizes easily) eluted first, the trans acid (2-((2R,3S,8R,8aS)-3-hydroxy-8,8a-dimethyl-1,2,3,4,6,7,8,8a-octahydronaphthalen-2-yl)acetic acid or it's enantiomer) eluted afterwards. This crude trans acid was heated with (S)-(−)-methylbenzylamine (1.60 g, 13.2 mmol) and 25 mL isopropanol. The solution was stirred at rt overnight, and the resulting suspension was filtered, the solid being washed with some isopropanol-ethyl acetate (1/1). Yield 0.35 g of the (S)-(−)-MBA-salt.

Both portions of the (S)-(−)-MBA-salt (2.31 g) were combined and recrystallized from 80 mL isopropanol to yield 1.65 g of the (S)-(−)-MBA-salt.

Example 21 Synthesis of Enantiomerically Pure EPD and its Enantiomer

The acid of the (S)-(−)-MBA-salt obtained according to Example 20 was liberated from the amine by washing and extraction and continued in subsequent reactions as described in Examples 14-17. Finally, EPD was obtained as determined by H-NMR and chiral HPLC as described herein-above.

The acid of the (R)-(+)-MBA-salt obtained according to Example 20 was liberated from the amine and continued in subsequent reactions as described in Examples 14-17. Finally, the enantiomer of EPD was obtained as determined by H-NMR and chiral HPLC as described herein-above.

The invention claimed is:
1. A method for the preparation of EPD or an analogue thereof according to formula I

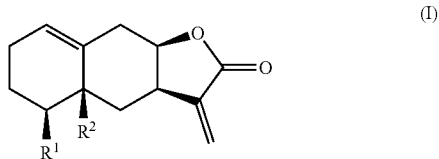

wherein $R^1$ and $R^2$ are independently selected from $R^3$, $SR^3$, $SO_2R^3$, $N(R^3)_2$, $C(O)NR^3$, $NC(O)R^3$, $OR^3$, $CO_2R^3$, $OC(O)R^3$, Cl, F, Br or I, and;
$R^3$ is selected from H, $C_1$-$C_8$ hydrocarbyl or poly(alkene oxide);
said method comprising converting an intermediate compound of formula II

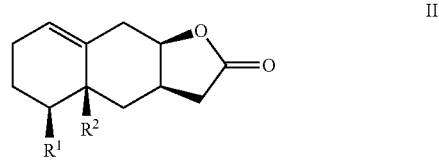

to EPD or an analogue of formula I by one or more steps comprising methylenation.
2. The method according to claim 1, comprising reducing a compound of formula III

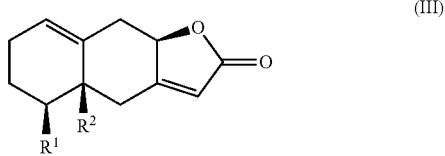

to the intermediate compound of formula II.

3. The method according to claim 2, further comprising converting a compound of formula IIa (IIa)

to a compound of formula III.

4. The method according to claim 3, wherein converting the compound of formula IIa to the compound of formula III comprises introducing a leaving group LG to form a compound of formula IIa-LG, (IIa-LG)

followed by eliminating the leaving group to form the compound of formula III.

5. The method according to claim 4, wherein the leaving group is selected from the group consisting of selenium, halide, ester or sulfonate.

6. The method according to claim 4, wherein the leaving group is selected from the group consisting of selenium or halide.

7. The method according to claim 4, wherein the leaving group is selected from the group consisting of bromide, chloride, or iodide.

8. The method according to claim 2, wherein reducing the compound of formula III to the intermediate compound of formula II is carried out with an hydride.

9. The method according to claim 2, wherein reducing the compound of formula III to the intermediate compound of formula II is carried out with a borohydride.

10. The method according to claim 2, wherein reducing the compound of formula III to the intermediate compound of formula II is carried out with sodium borohydride.

11. The method according to claim 3, further comprising converting a compound of formula V to the compound of formula IIa, (V)

wherein $R^5$ is independently selected from H, $C_1$-$C_6$ alkyl or a cation selected from ammonium, an alkali metal ion, or an alkaline earth metal ion.

12. The method according to claim 3, further comprising converting a compound of formula V,

V to the compound of formula IIa through an intermediate compound of formula VI, (VI)

wherein $R^6$ is independently selected from H, $C_1$-$C_6$ alkyl or a cation.

13. The method according to claim 12, wherein the cation is ammonium, an alkali metal ion or an alkaline earth metal ion.

14. The method for the preparation of EPD or an analogue thereof according to claim 1, comprising the preparation of the intermediate compound of formula II according to the following method
(i) introducing a leaving group LG to a compound of formula IIa, IIa to form a compound of formula IIa-LG, (IIa-LG)

(ii) eliminating the leaving group of the compound of formula IIa-LG to form the compound of formula III, (III)

(iii) reducing the compound of formula III to form the intermediate compound of formula II.
15. The method of claim 1, for the preparation of EPD or an analogue thereof according to formula I
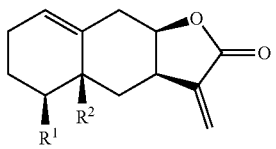
(I)
wherein $R^1$ and $R^2$ are independently selected from $OR^3$ or $R^3$ and;
$R^3$ is selected from H or methyl.
* * * * *

UNITED STATES PATENT AND TRADEMARK OFFICE
CERTIFICATE OF CORRECTION

Page 1 of 1

PATENT NO. : 12,018,006 B2
APPLICATION NO. : 16/620219
DATED : June 25, 2024
INVENTOR(S) : Caroline Van Haaften It is certified that error appears in the above-identified patent and that said Letters Patent is hereby corrected as shown below:

In the Specification

Column 2, Line 64, "$CO_2R$" should be --$CO_2R^3$--.

Column 9, Line 64, "$CO_2R^4OC(O)R^4$" should be --$CO_2R^4, OC(O)R^4$--.

Column 10, Line 52, "OR" should be --$OR^3$--.

Column 11, Line 58, "$CO_2R^4OC(O)R^4$" should be --$CO_2R^4, OC(O)R^4$--.

Column 17, Line 49, "3% h" should be --3½ h--.

Column 17, Line 60, "31 h" should be --3½ h--.

Column 22, Line 3, "(4)-one" should be --(4H)-one--.

Column 22, Line 44, "(3)-one" should be --(3H)-one--.

Signed and Sealed this
Twenty-first Day of January, 2025

Coke Morgan Stewart
*Acting Director of the United States Patent and Trademark Office*